United States Patent [19]

Saksena et al.

[11] Patent Number: 5,703,079
[45] Date of Patent: Dec. 30, 1997

[54] TETRAHYDROFURAN ANTIFUNGALS

[75] Inventors: Anil K. Saksena, Upper Montclair; Viyyoor M. Girijavallabhan, Parsippany; Raymond G. Lovey, West Caldwell; Russell E. Pike, Stanhope; Haiyan Wang, Dayton; Yi-Tsung Liu, Morris Township; Ashit K. Ganguly, Upper Montclair; Frank Bennett, Piscataway, all of N.J.

[73] Assignee: Schering Corporation, Kenilworth, N.J.

[21] Appl. No.: 460,400

[22] Filed: Jun. 2, 1995

Related U.S. Application Data

[63] Continuation-in-part of Ser. No. 171,083, filed as PCT/US94/14236, Dec. 20, 1994, abandoned.

[51] Int. Cl.$^6$ ............... A61K 31/495; C07D 405/14
[52] U.S. Cl. ........................... 514/252; 544/366
[58] Field of Search ............... 544/366; 514/252

[56] References Cited

U.S. PATENT DOCUMENTS

| | | | |
|---|---|---|---|
| 4,791,111 | 12/1988 | Heeres et al. | 514/252 |
| 5,039,676 | 8/1991 | Saksena et al. | 514/254 |

FOREIGN PATENT DOCUMENTS

| | | |
|---|---|---|
| 0539938A1 | 5/1993 | European Pat. Off. |
| WO 89/04829 | 6/1989 | WIPO |

OTHER PUBLICATIONS

Sinkula in *Annual Reports Medicinal Chemistry* vol. 10, Chapter 31, pp. 306–315 (1975).

Primary Examiner—Emily Bernhardt
Attorney, Agent, or Firm—Thomas D. Hoffman

[57] ABSTRACT

A compound represented by the formula I

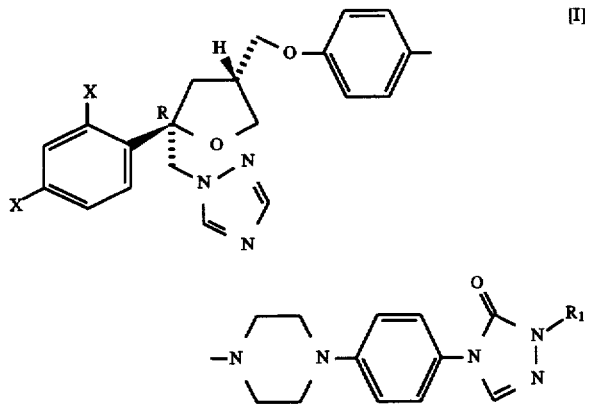

wherein X is independently both F or both Cl or one X is independently F and the other is independently Cl; $R_1$ is a straight or branched chain ($C_3$ to $C_8$) alkyl group substituted by one or two polyetyher ester groups (e.g., a polyether ester convertible in vivo into a hydroxy group) thereof or a pharmaceutically acceptable salt thereof and pharmaceutical compositions thereof useful for treating and/or preventing fungal infections are disclosed.

9 Claims, No Drawings

TETRAHYDROFURAN ANTIFUNGALS

CROSS-REFERENCE TO RELATED APPLICATIONS

This is a continuation-in-part application of International Application No. PCT/US94/14236, filed 20 Dec. 1994 which is a continuation-in-part of U.S. patent application Ser. No. 08/171,083, filed Dec. 21, 1993 now abandoned.

BACKGROUND OF THE INVENTION

This invention relates to tetrahydrofuran antifungals, (2R-cis)-4-[4-[4-[4-[[(5-(2,4-dihalophenyl)-tetrahydro-5-(1H-1,2,4-triazol-1-ylmethyl)-tetrahydrofuran-3-yl]methoxy] phenyl]-2,4-dihydro-2-[mono- or dihydroxy-substituted ($C_3$–$C_8$) alkyl]-3H-1,2,4-triazol-3-one substituted antifungals, esters, ethers and salts thereof, pharmaceutical compositions containing them, and methods of treating and/or preventing antifungal infections in hosts, including warm-blooded animals, especially humans with such tetrahydrofuran antifungals.

International Publication Number WO 89/04829, published 1 Jun. 1990 and U.S. Pat. No. 5,039,676 (A. K. Saksena et al.) discloses (±) cis and (±) (trans antifungal compounds represented by the formula

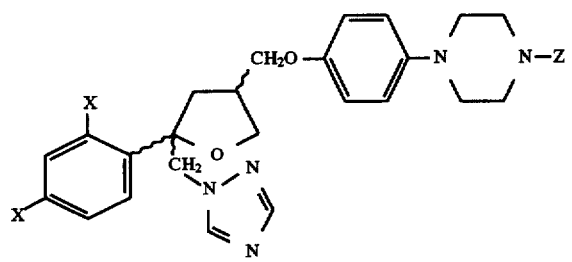

wherein X=F, Cl; Z=loweralkyl, (C2–C8) alkanoyl or phenyl substituted by 2-loweralkyl-3-oxo-1,2,4-triazol-4-yl, e.g., (±)-cis and (±)-trans-1-[4-[[2-(2,4-difluorophenyl)-2-[(1H-1,2,4-t riazol-1-yl)methyl] tetrahydro-4-furanyl]methoxy]phenyl]-4-(1-methylethyl)piperazine. However, WO 89/04829 does not disclose the compounds of this invention.

Commonly-owned European Patent Publication No. 05399381, published 5 May 1993 discloses, for example, [(5R)-cis-4-[4-[4-[[5-(2,4-dihalophenyl)-5-(1H-1,2,4-triazol-1-ylmethyl) tetrahydrofuran-3-7yl]methoxy]phenyl]-1-piperazinyl]pheynyl)-2,4-dihydro-2-($C_1$–$C_{10}$)alkyl)]-3H-1,2,4-triazol-3-one antifungals but does not disclose the compounds of this invention.

Janssen U.S. Pat. No. 4,791,111 discloses, for example, (+)cis-4-[4-[4-[4-[[2-2,4-dichlorophenyl)-2-(1H-1,2,4-triazol-1-ylmethyl)-1,3-dioxolan-4-yl]methoxy]phenyl]-1-piperazinyl]-2,4dihydro-2-(2-hydroxy-1-methylpropyl)-3H-1,2,4-triazol-3-one useful as an antimicrobial agent and having increased solubility, but does not disclose the compounds of this invention.

There is a need for broad-spectrum antifungal agents having increased solubility and having favorable activity profile for treating systemic fungal infections, especially Aspergillus, Candida, Cyrptococcus and opportunistic infections.

SUMMARY OF INVENTION

The present invention provides compounds represented by formula I

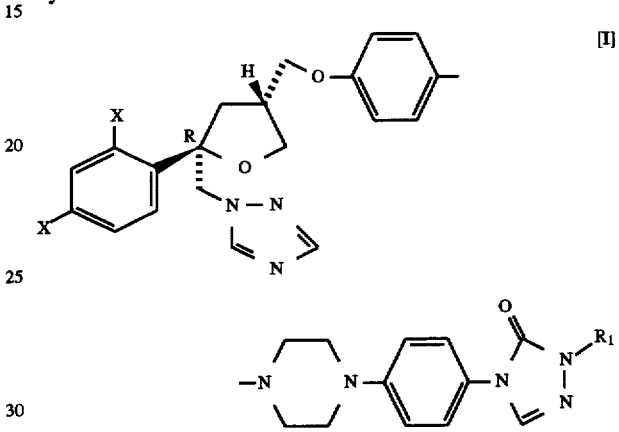

wherein X is independently both F or both Cl or one X is independently F and the other is independently Cl;

$R_1$ is a straight or branched chain ($C_3$ to $C_8$) alkyl group substituted by one or two hydro moieties or stereoisomers thereof or by one or two groups convertible in vivo into hydroxy moieties or an ester or ether thereof, or a pharmaceutically acceptable salt thereof.

In a preferred aspect of the present invention, there is provided compounds represented by formula II

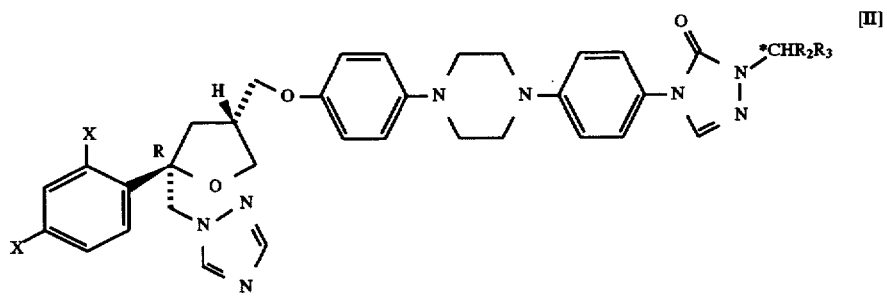

wherein X is independently both F or both Cl or one X is independently F and the other is independently Cl;

wherein $R_2$ is H or ($C_1$–$C_3$) alkyl and $R_3$ is ($C_1$–$C_3$) alkyl substituted by one hydroxy moiety or by a group convertible in vivo into a hydroxy moiety and the carbon with the asterisk (*) has the R or S absolute configuration; an ester or ether thereof or a pharmaceutically acceptable salt thereof.

In another preferred aspect, the present invention provides a compound represented by formula III

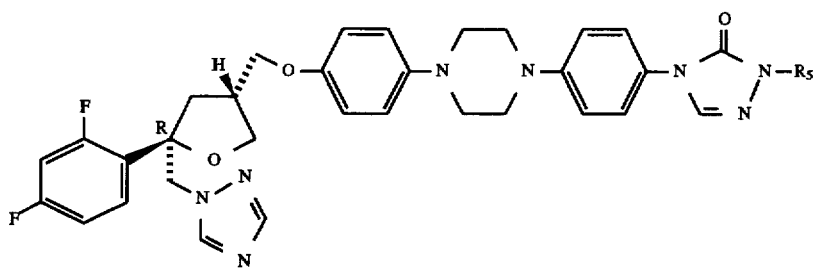

wherein R₅ is

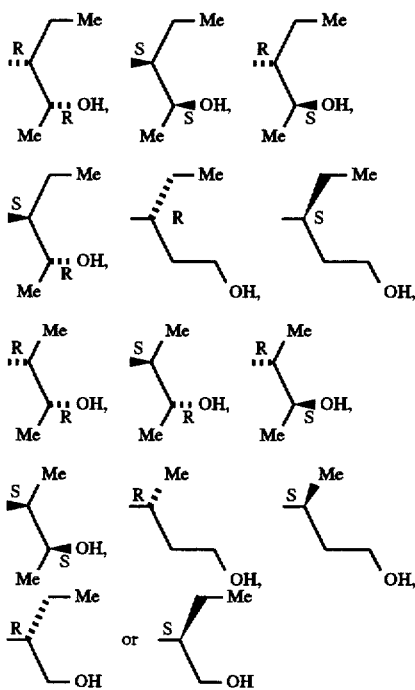

an ester or ether thereof or a pharmaceutically acceptable salt thereof.

Preferably the ester or ether is a group convertible in vivo into OH e.g. a polyether ester, phosphate ester or an amino acid ester.

In another aspect of the present invention there is provided a compound represent by the formula IV

DETAILED DESCRIPTION OF THE INVENTION AND OF THE PREFERRED EMBODIMENTS

The term "($C_3$–$C_8$) alkyl group substituted by one or two hydroxy moieties", as used herein means straight and branched chain alkyl groups of three to eight carbons including but not limited to methyl, ethyl, n- and iso-propyl, n-, sec-, iso- and tert-butyl, n-, sec-, iso-, tert and neo-pentyl n-, sec-, iso-, tert- and neo-hexyl, n-, sec-, iso-, tert- and neo-heptyl, n, sec- iso, tert- and neo-octyl, substituted by one or two hydroxy moieties and includes R and S stereoisomers of such ($C_3$–$C_8$) alkyl groups.

The term "($C_1$–$C_3$) alkyl substituted by one hydroxy moiety" means —$CH_2OH$, —*$CH(OH)CH_3$, —$CH_2CH_2OH$, —*$CH(OH)C_2H_5$, —*$CH_2CH(OH)CH_3$, and —$(CH_2)_3$—OH wherein the carbons with the asterisk(*) have the R or S absolute configuration.

The term "hydroxy-substituted $C_4$ or $C_5$ alkyl group" means —*$CH(C_2H_5)$*$CH(OH)CH_3$,—*$CH(C_2H_5)$ $CH_2CH_2OH$, —$(CH_2)_2$—*$CH(OH)C_2H_5$, —*$CH(CH_3)$ *$CH(OH)CH_3$, —*$CH(CH_3)$*$CH(OH)CH_3$ or —*CH ($C_2H_5$)$CH_2OH$ wherein each carbon with the asterisk (*) has the R or S absolute configuration.

The term "group convertible in vivo into OH" means a group transformable in vivo by e.g. hydrolysis and/or by an enzyme, e.g. an esterase into a hydroxyl group. Such groups include polyether esters, phosphate esters, sulfate esters, heterocyclic esters, alkanoate esters, alkenoate esters, amino acid esters and acid esters. Preferred groups convertible in vivo into a hydroxyl group are the polyether esters, phosphate esters and amino acid esters.

The term "ethers" means (a) straight and branched chain alkyloxy groups of one to twenty carbons, preferably of one to eight carbons, more preferably one to six carbons and (b) polyethylene glycols, e.g. PEG200 to PEG 10000, prefer-

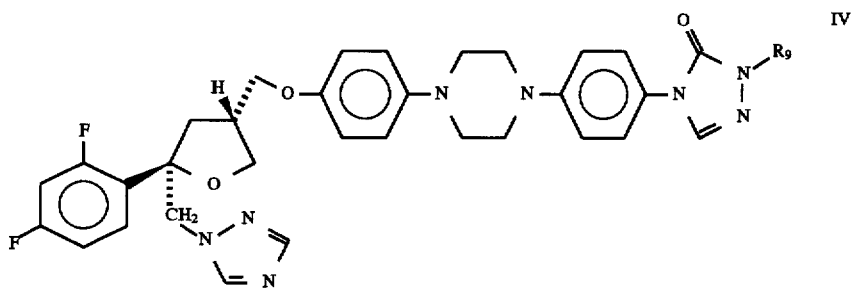

wherein $R_9$=—*$CH(C_2H_5)CH(R_6)CH_3$ or —*$CH(CH_3)CH$ ($R_6$)$CH_3$ wherein $R_6$ is OH, or a group convertible in vivo into OH or a pharmaceutically acceptable salt thereof.

ably PEG200 to 5000 or (c) aryl($C_1$–$C_6$) alkyloxy groups of the formula —O—(CHR₇)ₙ—Ar wherein R₇ is ($C_1$–$C_6$) straight and branched chain alkyl and n=0 to 6 preferably 1 to 3 and Ar is phenyl, phenyl substituted by halo, especially chloro and fluoro, or by nitro, cyano and trihalomethyl especially trifluoromethyl. Most preferred ether groups include methoxy and benzyloxy.

The term "esters" means (a) polyether esters (b) phosphate esters (c) heterocyclic esters (d) alkanoate and alkenoate esters (e) amino-acid esters (f) acid esters and (g) sulfate esters.

The term "polyether esters" as used herein means those polyether esters represented by the formula

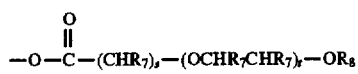

wherein
- $R_7$ is as defined herein and s is an integer from 1 to 6, preferably s=1 to 3 and more preferably s=1; t is an integer from 1 to 6; preferably t is 1 to 3, more preferably t is 2 or 3.
- $R^8$ is $R_7$ or $-(CHR_7)_s-CO_2R_7$; preferably $R_8$ is $CH_3$ or $C_2H_5$ or $-CH_2CO_2H$ or $-CH_2CO_2CH_3$. Typically suitable polyether esters include $-COCH_2O(CH_2CH_2O)_1CH_3$; $-COCH_2O(CH_2CH_2O)_2CH_3$, and $-COCH_2O(CH_2CH_2O)_3CH_3$; a compound represented by the formula IV wherein $R_6$ is a polyether ester group convertible in vivo into OH and the carbons with the asterisk (*) have the R or S absolute configuration, or a pharmaceutically acceptable salt thereof.

The polyether ester, $R_6$, is represented by the formula:

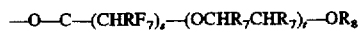

wherein $R_7$ is H or ($C_1$–$C_6$) straight or branched chain alkyl group, $R_8$ is $R_7$ or

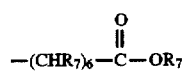

and s is 1 to 6 and t is 1 to 6;

Preferred polyether ester compounds include:

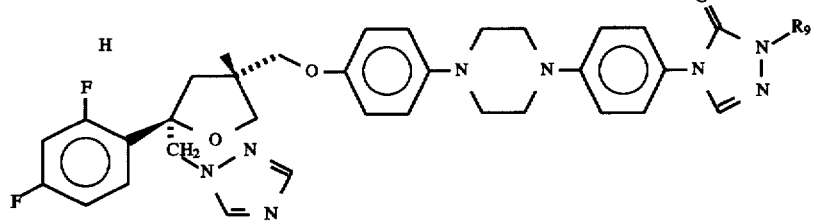

wherein $R_9$=—$CH(C_2H_5)CH(R_6)CH_3$ or —$CH(CH_3)CH(R_6)CH_3$

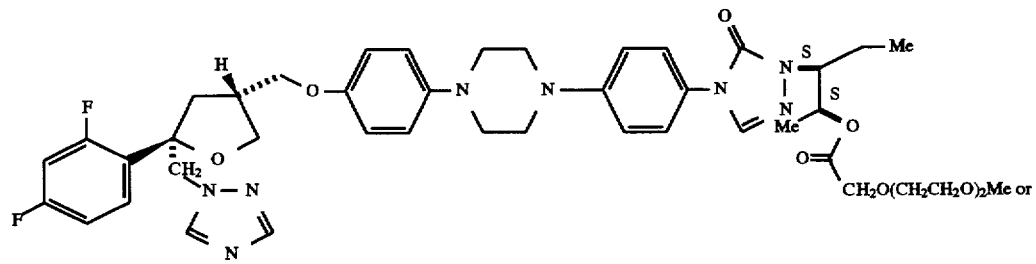

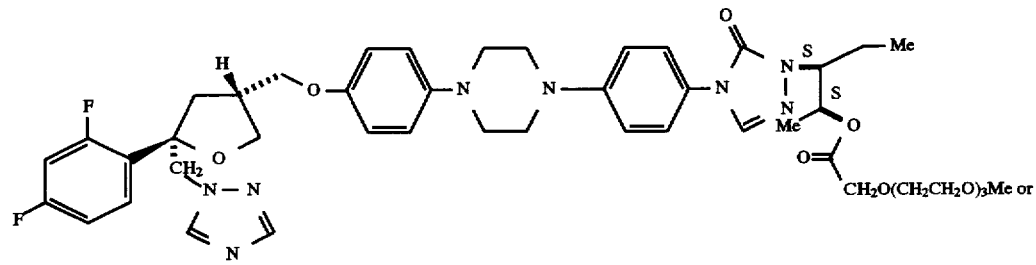

or a pharmaceutically acceptable salt thereof.

The term "phosphate esters" as used herein means those phosphate acids esters represented by the formula $$-O-[C(=O)]_z-(CHR_7)_n-(O)_m-P(=O)-(OW)_2$$

or $$-O-[C(=O)]_z-(CHR_7)_n-\text{Ph}-(CHR_7)_f-(O)_m-P(=O)(OW)_2,$$

wherein z is 0 or 1; $R_7$ is as defined herein above and preferably is H; n and f are independently an integer from 0 to 6, m is 0 or 1 and W is H, $CH_2Ar$ or

[phenol structure with OH]

and wherein Ar is as defined herein above. Typically suitable phosphate acids and esters include $$-O-P(=O)-(OCH_2C_6H_5)_2, \quad -O-P(=O)-(OH)_2,$$

$$-O-P(=O)(OH)-O-\text{Ph}-OH, \quad -O-C(=O)-(CH_2)_n-O-P(=O)(OH)_2$$

wherein m=n=1 to 4; or $$-O-C(=O)-CH(CH_3)-O-P(=O)(OH)_2$$

and pharmaceutically acceptable salts thereof.

The term "heterocyclic ester" as used herein means heterocyclic esters represented by the formula $$-O-C(=O)-(CHR_7)_w-N\begin{pmatrix}(CHR_7)_q\\(CHR_7)_{q'}\end{pmatrix}Y$$

wherein $R_7$ is as defined herein above, W is an integer of from 1 to 5 preferably W is 1 to 3; q and q' are independently 1 to 4, and q+q' are preferably equal to 2, 3, 4, or 5, and Y is $CHR_7$, —O—, NH, $NR_7$, S, SO or $SO_2$ Typically suitable heterocyclic esters include $$-OC-CH_2-N\bigcirc,$$

$$-OC-CH_2-N\bigcirc NH,$$

$$-OC-CH_2-N\bigcirc S,$$

$$-O-C-CH_2-N\bigcirc SO,$$

$$-OC-CH_2-N\bigcirc SO_2,$$

$$-O-C-CH_2-N\bigcirc N-CH_3,$$

$$-OC-CH_2-N\bigcirc O, \text{ and}$$

$$-OC-CH_2-N\bigcirc.$$

The term "alkanoate and alkenoate esters" as used herein means straight or branched chain alkanoate or alkenoate groups optionally substituted by a hydroxy or ether moiety or mixtures of such alkanoates or alkenoates.

Preferred alkanoate esters include acetate to decanoate, especially acetate to butanoate. Preferred hydroxy substituted alkanoate ester include $C_1$ to $C_8$ alkanoate substituted one hydroxy moiety or one $C_1$–$C_6$ alkoxy group, especially

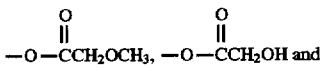

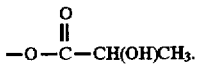

Preferred alkenoate esters are the $C_{10}$–$C_{20}$ alkenoates and include $C_{14}$ to C18 alkenoates, such as cis-7-hexadecenoate.

The term "amino acid ester" as used herein includes α-aminoalkanoyloxy, natural i.e., (L)-α-amino acid ester groups, e.g. the ester of glycine, i.e. $OCOCH_2NH_2$, peptides esters thereof, unnatural α-amino acid ester groups such as O—CO—CH($NH_2$)($CH_2$)$_3$ $CO_2H$, OCOCH($NH_2$)($CH_2$)$_2$ $NH_2$, OCOCH($NH_2$)($CH$)$_3NH_2$

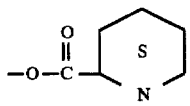

and

α-amino alkanoates represented by the formula —OCOCH ($NR_{20}R_{21}$)$R_{22}$ wherein $R_{20}$ and $R_{21}$ are independently hydrogen or ($C_1$–$C_8$) straight or branched chain alkyl groups or $R_{20}$ and $R_{21}$ together with N form a 4, 5 or 6 membered ring optionally substituted with $NR_{21}$, —O— or —S— and $R_{22}$ is H, $CH_3$, $CH_2OH$, $CH(OH)CH_3$, $CH_2SH$,

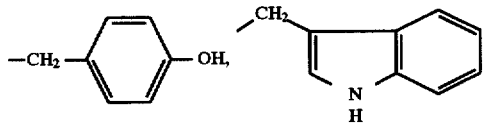

$CH_2 CONH_2$, —($CH_2$)$_2CONH_2$, $CH(CH_3)_2$, $CH(CH_3)_2$, $CH(CH_3)C_2H_5$, ($CH_2$)$_2SCH_3$, $CH_2$, $CO_2H$, ($CH_2$)$_2CO_2H$, ($CH_2$)$_4NH_2$, —$CH_2C_6H_5$,

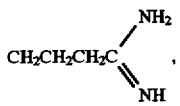

and pharmaceutically acceptable acid addition salts thereof, or ($C_1$–$C_8$) straight and bianched chain alkyl groups optionally substituted by hydroxyl or $NR_{20}R_{21}$. Preferred amino acid acids are the natural α amino acid groups, dipeptides and α-amino alkanoates wherein $R_{20}$ and $R_{21}$ are each $CH_3$. The most preferred amino acid esters are those derived from alanine, phenylanine, glycine, leucine, isoleucine and valine.

The term "acid ester" as used herein means those acid esters represented by the formula

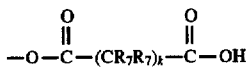

wherein $R_7$ is as defined herein above and k is an integer of from 1 to 8. Typically suitable acid esters include oxalic, malonic, succinic, glutaric and adipic acids as well as branched chain diacids such as

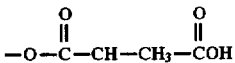

The term "ether" as used herein means ($C_1$–$C_6$) alkoxy or aryl ($C_1$–$C_6$) alkoxy which are conveniently made by the well known Williamson Synthesis of ethers. Typically suitable ether groups include methoxy and benzoxy.

The compounds of the present invention as well as the esters and ethers thereof exhibit broad spectrum antifungal activity in various in vitro assays against Candida, other yeasts, dematophytes, Aspergillus and opportunistic fungi. The in vitro antifungal activity tests were performed via conventional broth dilution methods in Sabouraud dextrose broth ("SDB") medium and Eagles Minimum Essential Medium ("EMEM") against a large number of fungi. Minimum Inhibitory Concentrations ("MICs") were measured after 24, 48 and 72 hour tests. In many cases, Minimum Fungicidial Concentrations ("MFCS") were measured after 48 and 72 hours.

The term "opportunistic fungi" include Crytococcus, Histoplasma, Blastomyces, Coccidioides, Fusarium, Mucor, Paracoccidioides, Fonsecaea, Wangiella, Sporothrix, Pneumocystis, Trichosporon as shown by in vivo activity in an appropriate animal species e.g. mouse, rat or rabbit. The compounds of the inventions are expected to exhibit activity against many genera and species of protoza, bacteria, gram negatives, gram positives, anaerobes, including Legionella Borrelia, Mycoplasma, Treponema, Gardneralla, Trichomononas and Trypanosoma The preferred compounds of formula III wherein $R_5$=hydroxy-substituted $C_4$ and $C_5$ alkyl groups, exhibited the following in vitro antifungal activity in SDB against 37 species of Aspergillus, flavus, fumigatus and other species: geometric mean MICs were in the range of $\leq 0.05$ to $\leq 0.81$ (mcg/ml) and geometric mean MFCs were in the range of 0.42 to $\geq 3.78$ mcg/ml.

The preferred compounds of formula III wherein $R_5$ is a hydroxy-substituted $C_5$ alkyl group exhibited (1) superior antifungal activity as measured by geometric mean MICs and MFCs in various in vitro assays against C. albicans (N=26), C. krusei (N=16), C. glabrata (N=9), C. tropicalis (N=4), C. stellatoidea (N=1), C. neoformans (N=3), and of the dermatophytes, T. rubrum, T. mentagrophytes, and T. tonsurans (N=6) (after 48 or 78 hours) compared to fluconazole as well as (2) superior anti-fungal activity in the following in vivo models: an Aspergillus flavus and fumigatus (four strains) in a pulmonary immuno-compromised mouse model (PO-1XDX4D) compared to other azoles e.g. itraconazole, and in a Candida albicans (four strains) systemic model with normal and compromised mice (PO-1XDX4D) compared to other azoles, e.g. fluconazole. The preferred compounds of formula IV wherein $R_9$ is a —*CH ($C_2H_5$)CH($R_6$)$CH_3$, wherein $R_6$ is a group convertible in vivo into OH exhibited superior antifungal activity comparable to the above listed preferred compounds of formula III wherein $R_5$ is a hydroxy-substituted $C_5$ alkyl group.

The in vivo oral antifungal activity of the compounds of the present invention were compared to azole antifungals, e.g., fluconazole in an Aspergillus pulmonary infection model in mice. The procedure of David Loebenberg et al. entitled "In vitro and In vivo Activity of Sch 42427, The Active Enantiomer of the Antifungal Agent Sch 39304", Antimicrobial Agents and Chemotherapy, (1992), 36, 498–501 was used. The Aspergillus flavus pulmonary model is also described in European Patent Application No. 0539, 938 A1 published on 5 May 1993.

The preferred compounds of formula III exhibited superior antifungal in vitro activity in SDB against 37 species of Aspergillus with (a) geometric mean MICs of ≦0.05 to ≦0.81 compared to fluconazole (geometric mean MIC≧32 and (b) with geometric mean MFCs of ≦0.42 to ≧3.78 compared to fluconazole (geometric mean MFC≧32).

The Tables Q, R, and S hereinbelow display the superior in vitro antifungal activity of three preferred compounds of formula III compared to fluconazole. Table Q displays such antifungal activity as the percentage of strains of various fungi with MICs≦1 mcg/ml for the three preferred compounds of formula III compared to fluconazole. Table R displays the antifungal activity as the percentage of the same strains with MFCs≦1 mcg/ml. Table S displays the in vitro MIC 90 values for the three preferred compounds of formula III against the same organisms listed in Tables Q and R.

The most preferred compound of formula III where $R_5$=

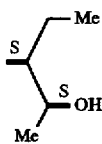

showed consistently higher serum levels in mice, rats, dogs and monkeys following oral dosing with a methyl cellulose formulation compared to azoles of similiar structure and also exhibited very long serum half lives following O.D. dosing with good tissue distribution. The above listed most preferred compound of formula III are not inducers of various cytochrome P-450 liver drug metabolizing enzymes after oral administration in an in vivo rat model,

TABLE Q

IN VITRO ANTIFUNGAL ACTIVITY FOR SELECTED COMPOUNDS OF FORMULA III[1]

| | | PERCENTAGES OF STRAINS WITH MICs ≦1 MCG/ML (MCG/ML) | | | |
| | | $R_4 =$ | | | |
| ORGANISMS | STRAINS | R,,,⟩—◀OH / Me S | S⟩—◀OH / Me S | S⟩--OH / Me R | FLZ[2] |
|---|---|---|---|---|---|
| Aspergillus | 37 | 100 | 100 | 100 | 0 |
| Candida albicans | 26 | 100 | 100 | 100 | 100 |
| Candida krusei | 16 | 100 | 100 | 100 | 0 |
| Candida tropicalis & stellatoidea | 5 | 100 | 100 | 100 | 100 |
| Candida glabrata | 9 | 22 | 22 | 33 | 0 |
| Cryptococcus neoformans | 3 | 100 | 100 | 100 | 0 |
| Dermatophytes | 6 | 100 | 100 | 100 | 100 |

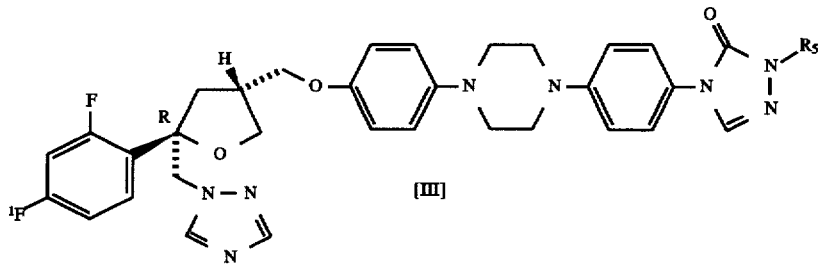

[2]FLZ = fluconazole

TABLE R

IN VITRO ANTIFUNGAL ACTIVITY FOR SELECTED COMPOUNDS OF FORMULA III[1]

| | | PERCENTAGES OF STRAINS WITH MFCs ≤1 MCG/ML (MCG/ML) $R_s =$ | | | |
|---|---|---|---|---|---|
| ORGANISMS | STRAINS | R,,, Me / OH S, Me | S, Me / OH S, Me | S, Me / ··OH R, Me | FLZ[2] |
| Aspergillus | 37 | 50 | 62 | 89 | 0 |
| Candida albicans | 26 | 100 | 100 | 100 | 100 |
| Candida krusei | 16 | 88 | 94 | 100 | 0 |
| Candida tropicalis & stellatoides | 5 | 100 | 100 | 100 | 100 |
| Candida glabrata | 9 | 22 | 22 | 22 | 0 |
| Cryptococcus neoformans | 3 | 100 | 100 | 100 | 0 |
| Dermatophytes | 6 | 67 | 83 | 100 | 0 |

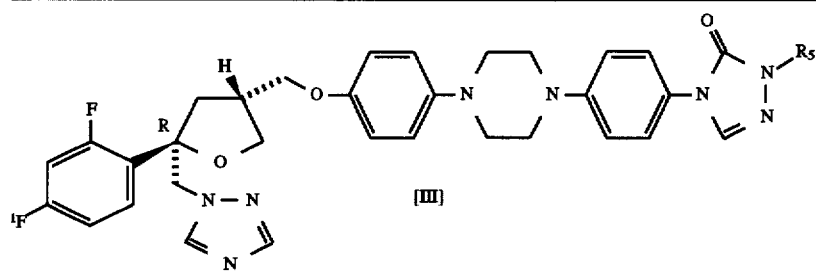

[III]

[2]FLZ = fluconazole

TABLE S

IN VITRO ANTIFUNGAL ACTIVITY FOR SELECTED COMPOUNDS OF FORMULA III[1]

| | | MIC 90 Values* (MCG/ML) $R_s =$ | | | |
|---|---|---|---|---|---|
| ORGANISMS | STRAINS | R,,, Me / OH S, Me | S, Me / OH S, Me | S, Me / ··OH R, Me | FLZ[2] |
| Aspergillus | 37 | .122 | .096 | .112 | 29.9 |
| Candida albicans | 26 | .274 | .174 | .139 | .887 |
| Candida krusei | 16 | .058 | .014 | .12 | 29.9 |
| Candida tropicalis & stellatoidea | 5 | .117 | .117 | .354 | .917 |
| Candida glabrata | 9 | 28.8 | 17.1 | 28.8 | 29.3 |

TABLE 5-continued

IN VITRO ANTIFUNGAL ACTIVITY FOR SELECTED COMPOUNDS OF FORMULA III[1]

| ORGANISMS | STRAINS | MIC 90 Values[a] (MCG/ML) $R_4 =$ | | | |
|---|---|---|---|---|---|
| | | R⋯⟨Me / ⫨OH-S⟩ Me | S⟨Me / ⫨OH-S⟩ Me | S⟨Me / ⋯OH-R⟩ Me | FLZ[2] |
| *Cryptococcus neoformans* | 3 | .05 | .007 | .101 | 25.9 |
| Dermatophytes | 6 | .165 | .101 | .707 | 29.4 |

[2]FLZ = fluconazole
[a]Minimum Inhibitory Concentrations for 90% of the strains

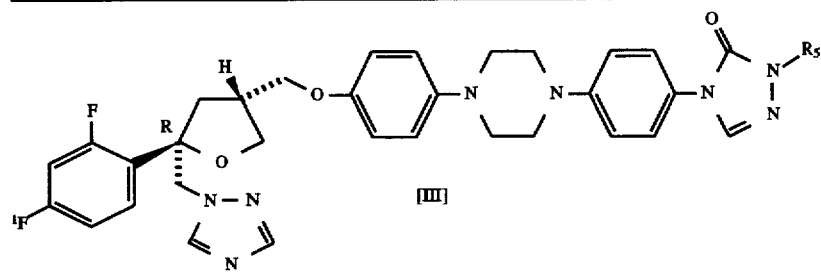

[III]

The preferred esters and ethers of the compounds of the present invention of formula IV are soluble and/or suspendible in an aqueous medium suitable for IV or oral administration and also exhibit superior in vivo antifungal activity against a broad range of fungi after oral and parenteral e.g. IV administration in mice, rats, dogs and monkeys. The preferred esters and ethers of the compounds of formula IV which are convertible in vivo into the corresponding alcohols have a solubility in aqueous medium of at least about 1 to 50 mg/ml, preferably greater than or equal to about 10 mg/ml and more preferably about 20 to about 50 mg/ml. The preferred esters and ethers of formula IV listed below wherein $R_9$ is:

IV $R_9$

M+ 905

$R_9$

M+ 841

-continued
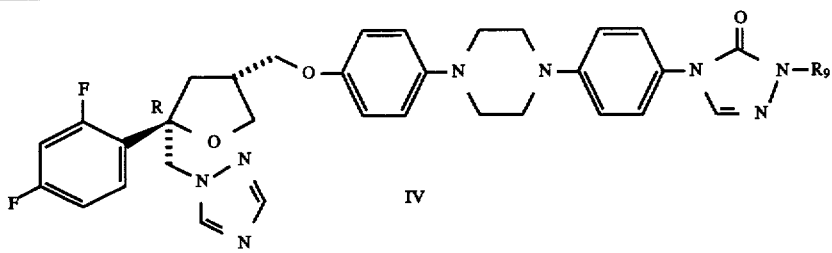
| $R_9$ | $R_9$ |
|---|---|
| 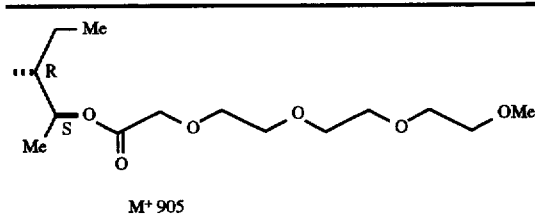<br>M+ 905 | 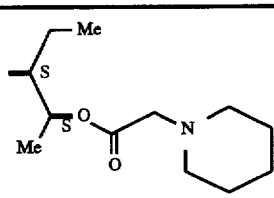<br>M+ 826 |
| 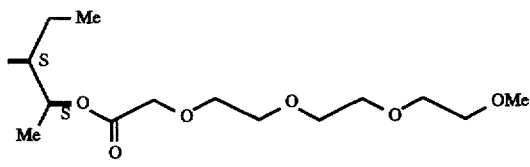<br>M+ 905 | 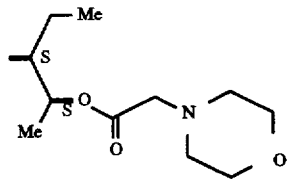<br>M+ 828 |
| 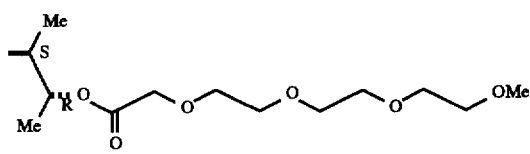<br>M+ 891 | 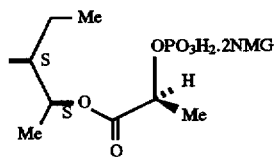<br>M+ 853.2 |
| 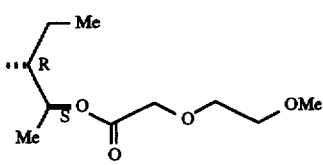<br>M+ 817 | 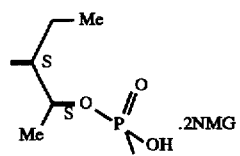<br>M+ 781.7 |
| 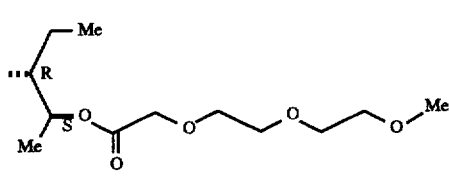<br>M+ 861 | 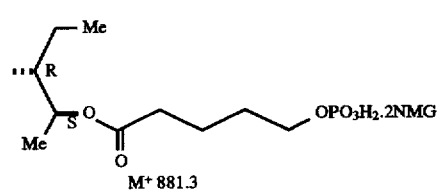<br>M+ 881.3 |
| 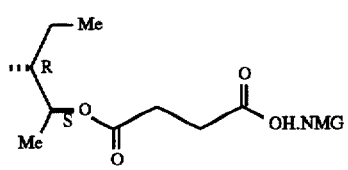<br>M+ 801 | 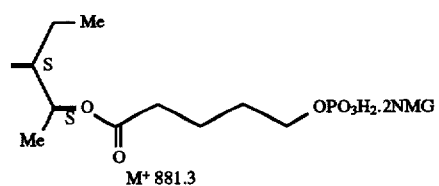<br>M+ 881.3 |

-continued
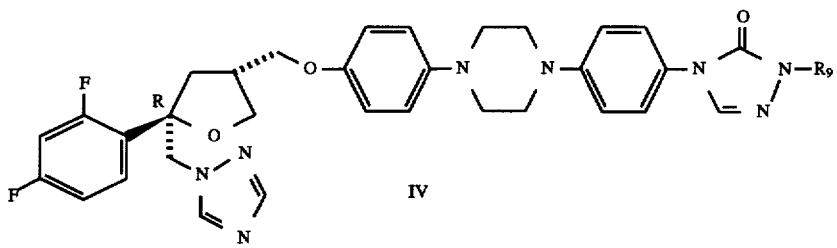
IV
| $R_9$ | $R_9$ |
|---|---|
|  | |

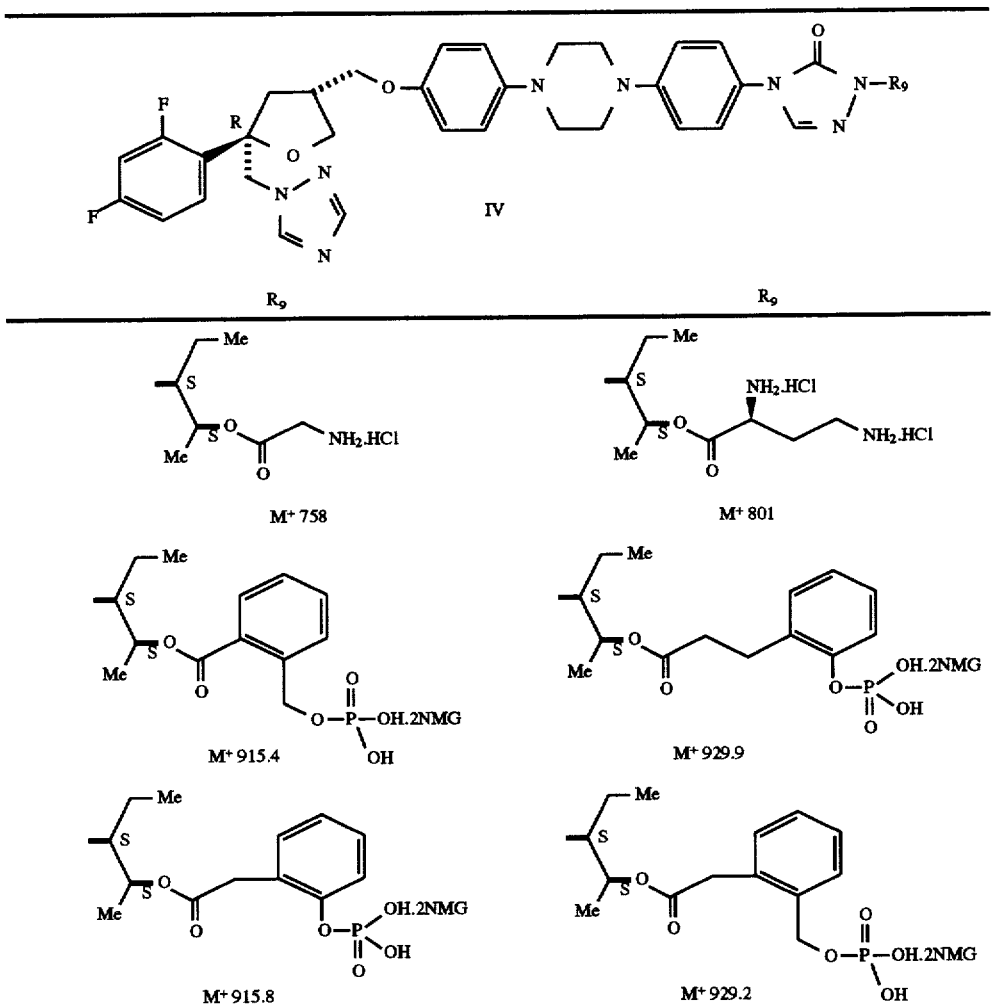

IV

The mass spectral data presented herein as M⁺ are parent ions which were determined by Fast Atom Bombardonment (FAB) technique and represent the [M + H]⁺, i.e. {molecular ion + 1} peaks.

The more preferred esters listed hereinabove are water soluble (eg >10 mg/ml) and readily convertible in vivo to the corresponding alcohols e.g. $R_5$ is

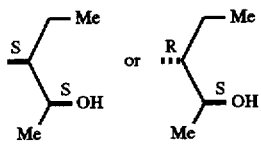

The most preferred esters are convertible in vivo into alcohols and include those of compounds of formula IV wherein $R_9$ is

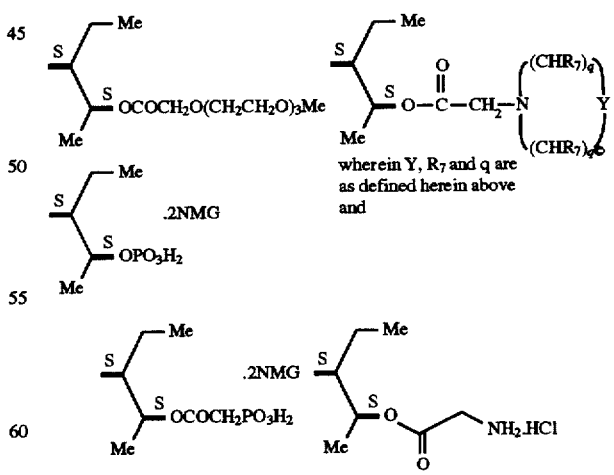

wherein Y, $R_7$ and q are as defined herein above and

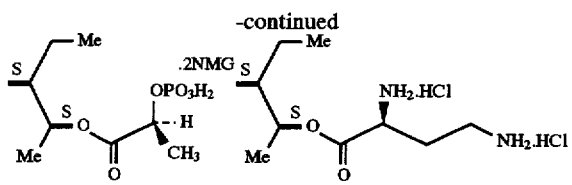

The antifungal compounds of this invention represented by formula I have the R absolute stereochemical configuration at the carbon in the tetrahydrofuran ring bearing the di-halophenyl and 1H,1,2,4-triazol-1-ylmethyl moieties, and the CH₂OY moiety has the "cis" stereochemical configuration relative to the 1H,1,2,4-triazol-1-ylmethyl moiety. See the formula I hereinbelow.

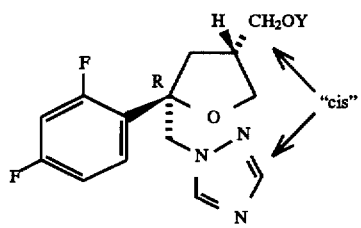

and Y=

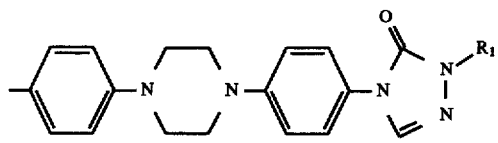

wherein $R_1$ is a straight or branched chain ($C_3$–$C_8$) alkyl group substituted by one or two hydroxy groups, which preferably exists as a single stereoisomer, but mixtures of stereoisomers are also contemplated as within the scope of this invention.

The compounds of formula I are generically but not specifically disclosed as the "cis" series, type ii, at col. 9 lines 59–68 of Saksena et al. U.S. Pat. No. 5,039,676 and Example 68 at Col. 5, line 16 to col. 52, line 44.

GENERAL SYNTHETIC PREPARATIONS

The compounds of this invention may be prepared by use of the sequence of steps illustrated in the following Schemes I–V. In Scheme I, compound 3 is readily prepared from commercially available compound 1 according to Examples 1a, 1b and 1c. Compound 4 is prepared by reaction of L(+)-diethyl tartarate ("L-DET") and molecular sieves in the presence of titanium tetra-isopropoxide (i-PrO)₄Ti in an aprotic solvent, such as methylene chloride, at a temperature 0° to −35° C. See for Example, T. Katsuki, K. B. Sharpless, J. Am. Chem. Soc,. 102, 5974 (1980); and 103, 464 (1981). An oxidizing agent, e.g. tert-butylhydroperoxide ("TBHP") is added to this reaction mixture (step d of Scheme I). Compound 3 is added and the compound of formula 4 (when L(+)-diethyl tartarate is used) is produced. Reaction of compound 4 with 1H-1,2,4-triazole in the presence of strong base, e.g., NaH in an aprotic solvent, such as DMF, at 0°–80° C. provides the diol compound of formula 5. The primary hydroxy group in compound 5 is converted into a leaving group, e.g., mesylate or tosylate (compound 6) by reaction of 5 with, for example, mesyl chloride ("MsCl"), in an aprotic solvent, e.g., methylene chloride in the presence of base, e.g., triethylamine ("Et₃N"). Compound 6 is treated with strong base, e.g., sodium hydride (NaH) in an aprotic solvent, e.g., DMF at room temperature to give oxirane compound 7. Reaction of 7 with diethyl malonate in the presence of strong base, e.g., sodium hydride in an aprotic solvent, e.g., DMSO at 25°–75° C. provides the lactone 8. Reduction of 8 with a metal hydride, e.g., lithium borohydride (LiBH₄) in an alcohol, e.g., ethanol (EtOH), provides the triol 9. Conversion of the two primary alcohols of 9 into leaving groups (mesylates or tosylates) by reaction of 9 with excess tosyl chloride in an aprotic solvent, e.g., THF, in the presence of base, e.g., Et₃N, provides ditosylate 10. Compound 10 is contacted with strong base, e.g., NaH, in an aprotic solvent such as toluene at elevated temperatures of 100°–120° C. to provide a mixture of two tosylates (cis and trans) which are separated by chromatography to yield to the cis-tosylate 11. Reaction of compound 11 with alcohols HOY in the presence of strong base, such as NaH in an aprotic solvent, such as DMSO at a temperature of 25°–75° C. provides compounds of formula I.

Scheme II provides an alternative reaction sequence to obtain compounds of the present invention. Reaction of compound 11 with the commercially available compound 12 in the presence of NaH gives compound 13. Hydrolysis of N-acetyl group in 13 is accomplished with a strong base such as NaOH in the presence of n-BuOH to provide compound 14. It should be made clear that instead of N-acetyl group in compound 12, any other base labile groups such as N-formyl, N-benzoyl, etc., can also be used to provide corresponding N-formyl and N-benzoyl derivatives of compound 13. Reaction of 13 with p-chloronitrobenzene in the presence of a hydrochloric acid scavenger such as K₂CO₃ provides the nitro compound 15. Catalytic reduction of 15 in the presence of a platinum or palladium catalyst yields the amine 16. Treatment of 16 with phenylchloroformate in the presence of pyridine gives the urethane intermediate 17. Reaction of 17 with hydrazine yields the semicarbazide 18 which is cyclized in the presence of formamidine acetate to furnish the key triazolone 19. Alkylation of 19 according to Examples 19 and 20 provides the compounds of structure 20 including compounds of formula I wherein $R_1$ is defined as hereinabove.

Scheme III provides a stereospecific access to the cis-alcohol 26 and cis-tosylate 11 by application of enzyme chemistry. For Example, reaction of the triol 9 with ethyl acetate in the presence of porcine pancreatic lipase gives a single monoacetate 21. The remaining primary hydroxy group in 21 is protected by an acid labile group such as tetrahydropyranyl group to give a compound such as 22. Hydrolysis of the acetoxy group in 22 is accomplished with a base such a KOH which provides 23. The remaining steps are: (i) tosylation of compound 23 to provide 24; (ii) cyclization of 24 in the presence of NaH to provide 25; (iii) deprotection of THP ether in 25 using an acid catalyst such as p-toluene sulfonic acid (to give 26) followed by tosylation of the resulting 26 to furnish the key intermediate 11.

A detailed description of a preferred preparation of key intermediate is disclosed in commonly owned U.S. patent application Ser. No. 08/055,268, filed Apr. 30, 1993 and now U.S. Pat. No. 5,403,937, issued Apr. 4, 1995, which is hereby incorporated by reference.

SCHEME I
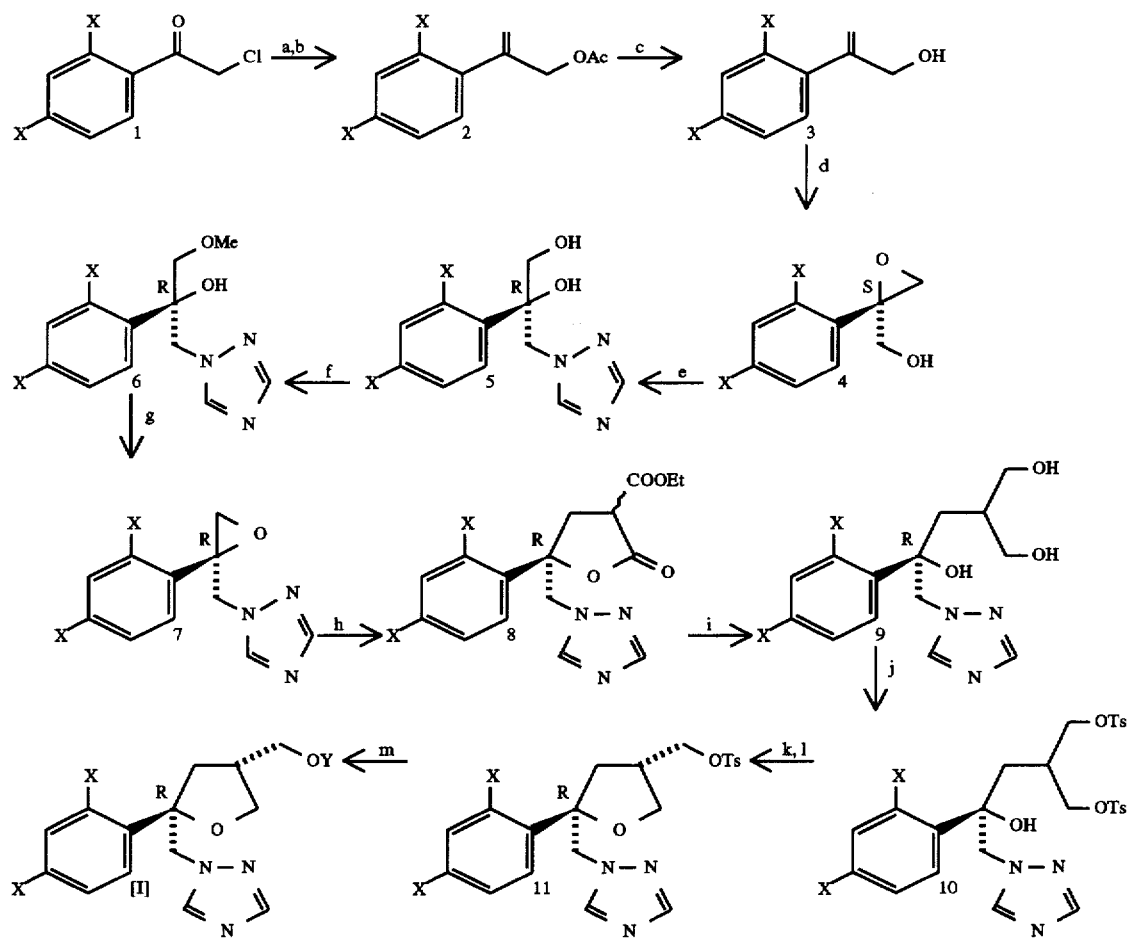
X = F or Cl
Reagents: (a) NaOAc; (b) Wittig Reaction; (c) KOH; (d) L-DET, TBHP, (i-Pr)₄Ti; (e) NaH, 1,2,4-triazole, DMF; (f) MsCl, Et₃N, CH₂Cl₂, 0–5° C.; (g) NaH, DMF; (h) NaH, diethylmalonate, DMSO, 50–55° C.; (i) LiBH₄, EtOH; (j) TsCl, Et₃N, DMAP, CH₂Cl₂-THF (1:1, v/v); (k) NaH, toluene, 100° C.; (l) Chromatography; (m) NaOY, DMSO.
SCHEME II
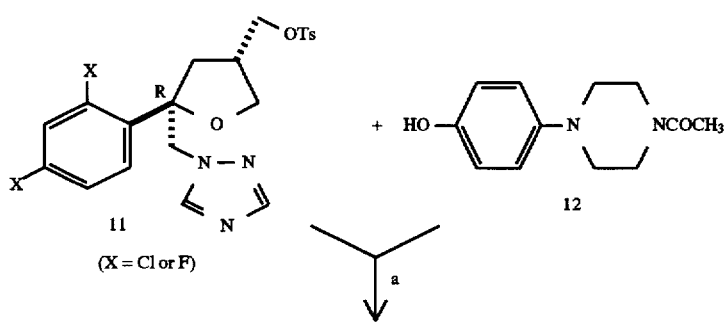

-continued
SCHEME II
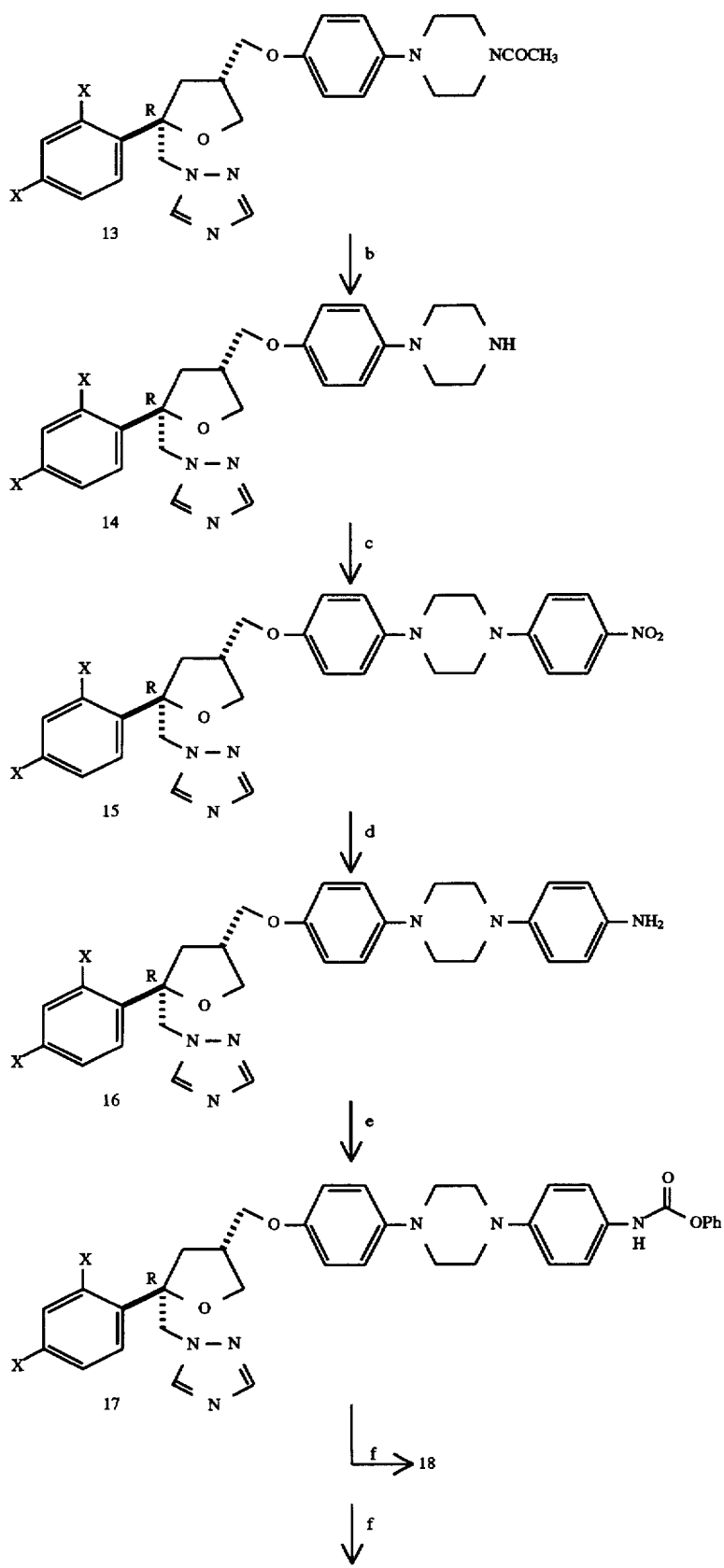

-continued
SCHEME II
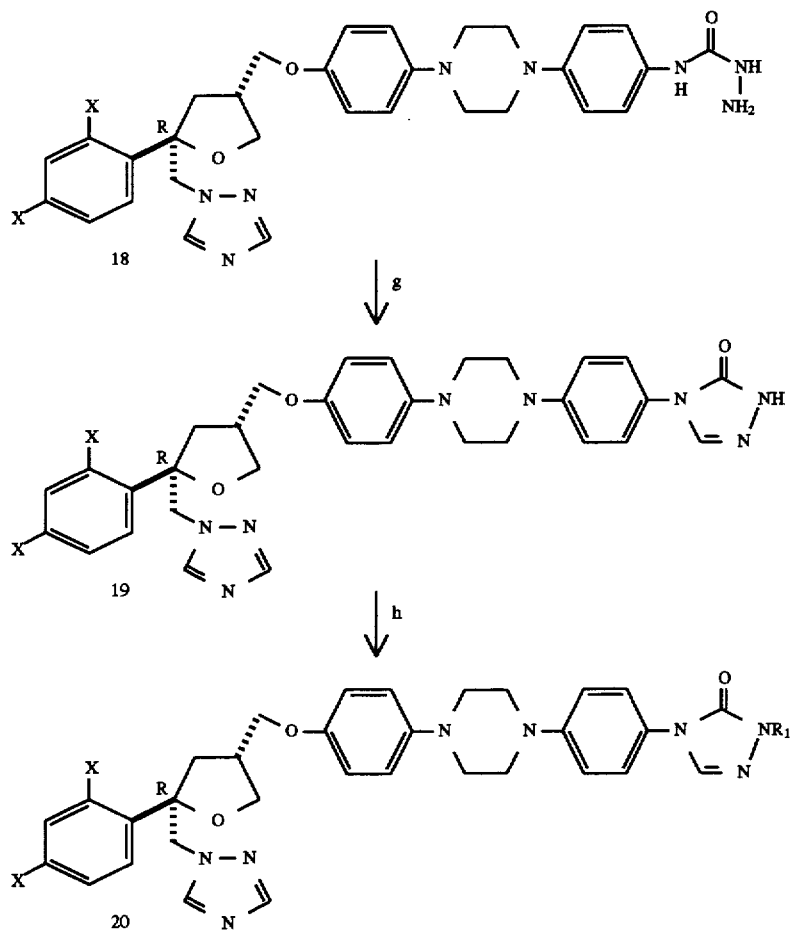
Reagents: (a) NaH, DMF; (b) NaOH, n-BuOH; (C) p-Cl—C$_6$H$_4$NO$_2$, K$_2$CO$_3$, DMSO; (d) H$_2$, Pt-C; (e) C$_6$H$_5$OCOCl, pyridine, CH$_2$Cl$_2$; (f) NH$_2$NH$_2$.H$_2$O, H$_2$O, dioxane; (g) formamidine acetate, DMF, 80° C.; (h) according to Examples 19 and 20.
SCHEME III
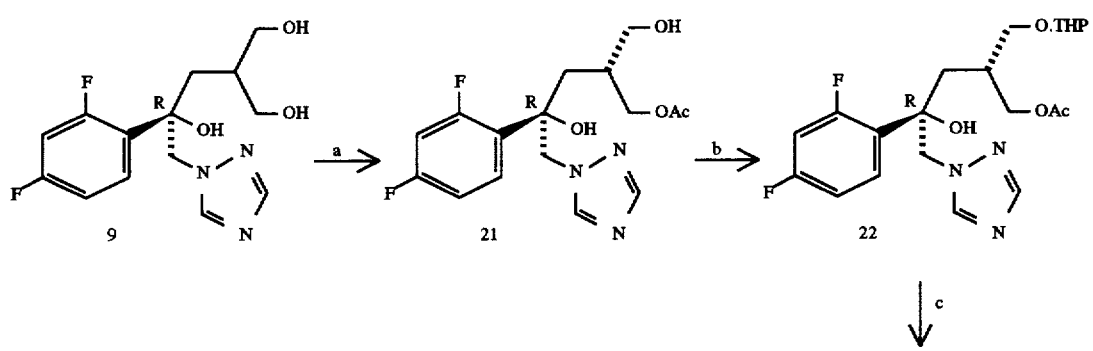

-continued
SCHEME III
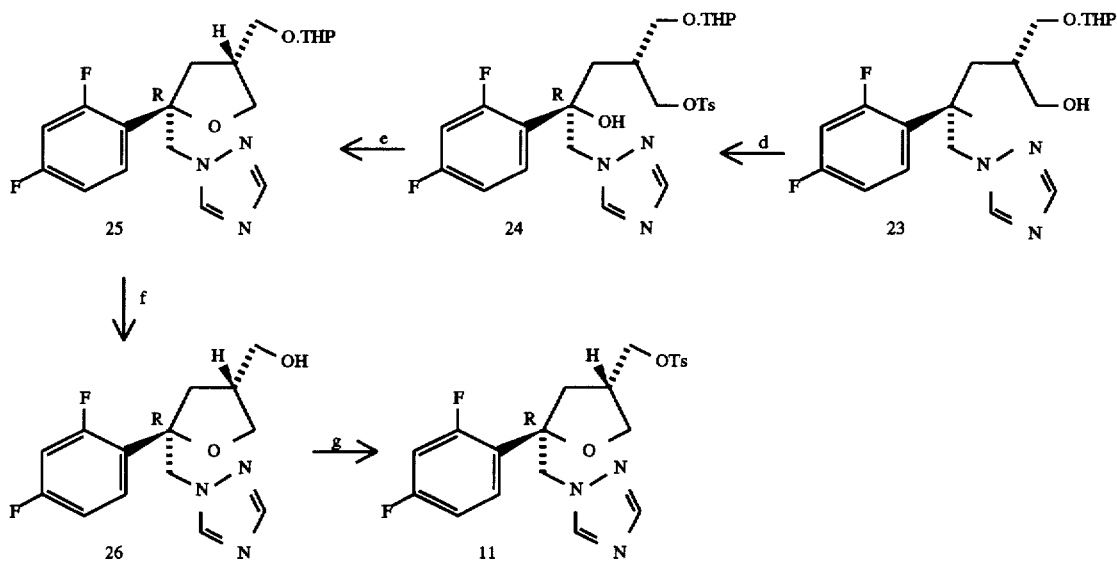
Reagents: (a) Porcine pancreatic lipase, EtOAc; (b) dihydropyran, H⁺, CH₂Cl₂; (c) KOH; (d) tosyl chloride, pyridine; (e) NaH, toluene; (f) H₂O, methanol, H⁺; (g) tosyl chloride, pyridine.
SCHEME IV
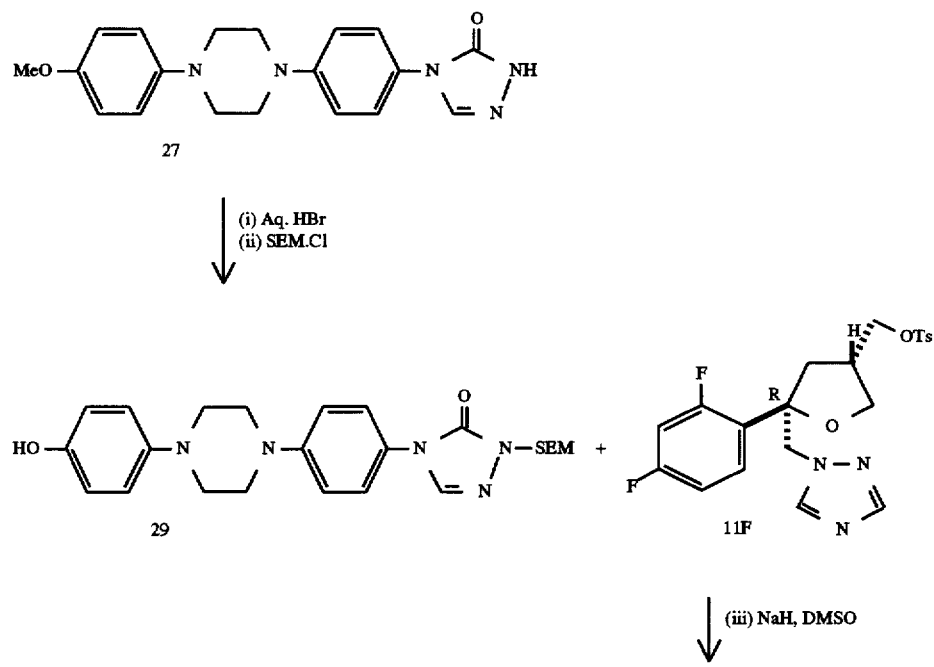

-continued
SCHEME IV
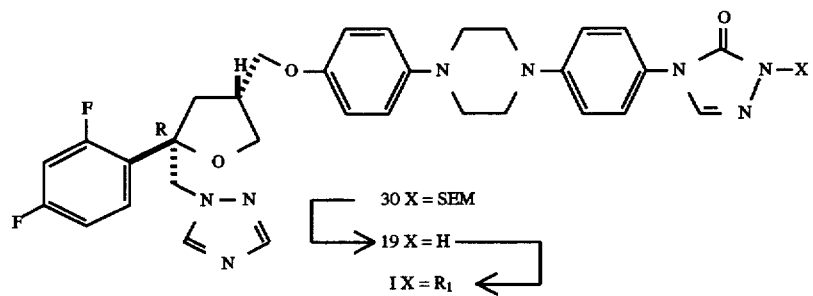
SCHEME V
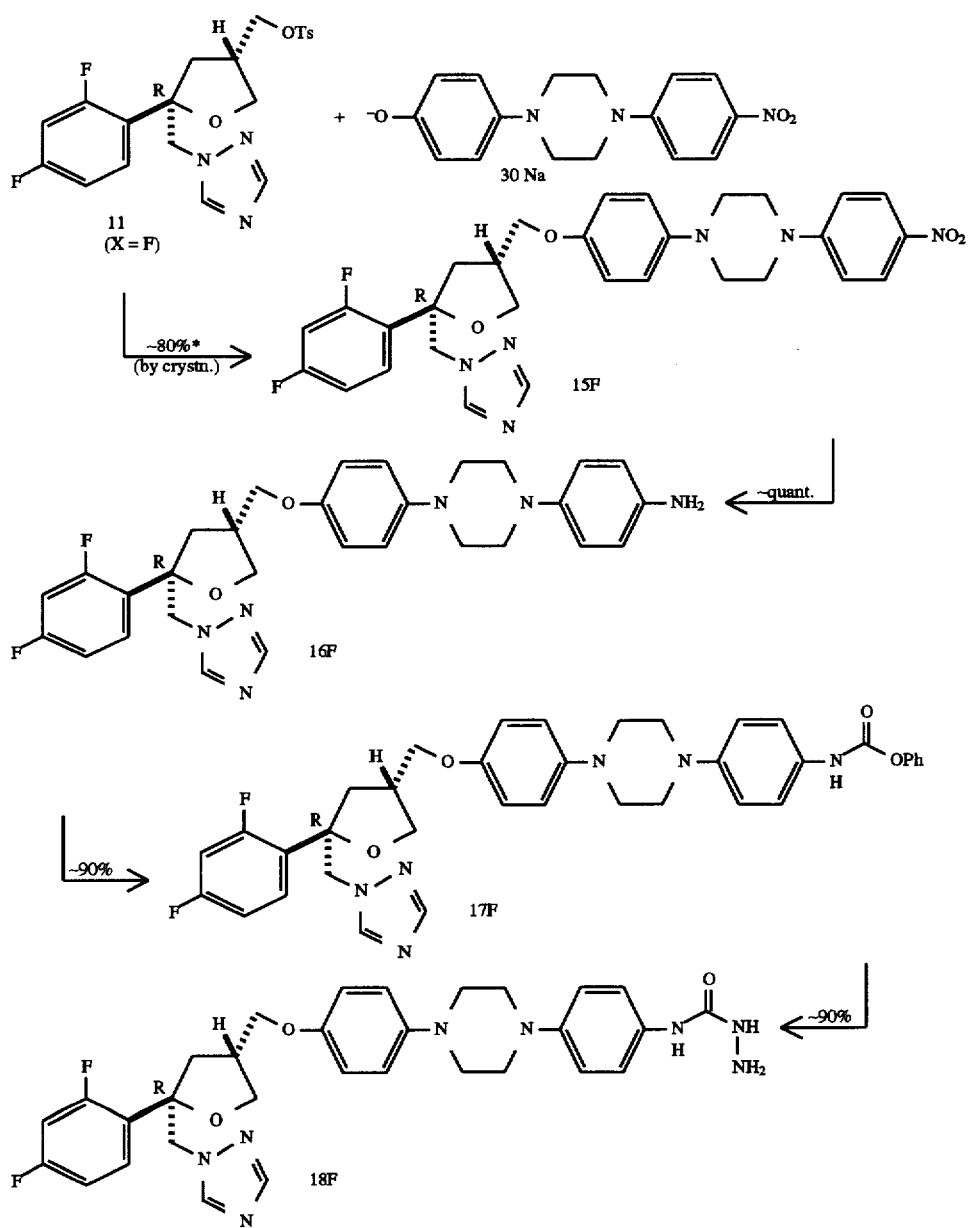

-continued
SCHEME V
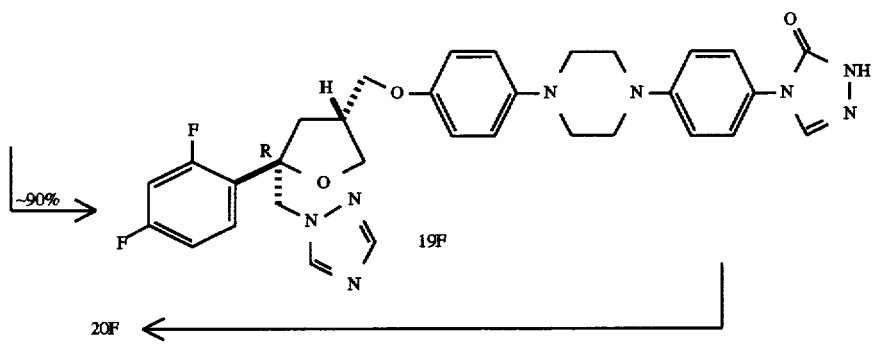
SCHEME VI
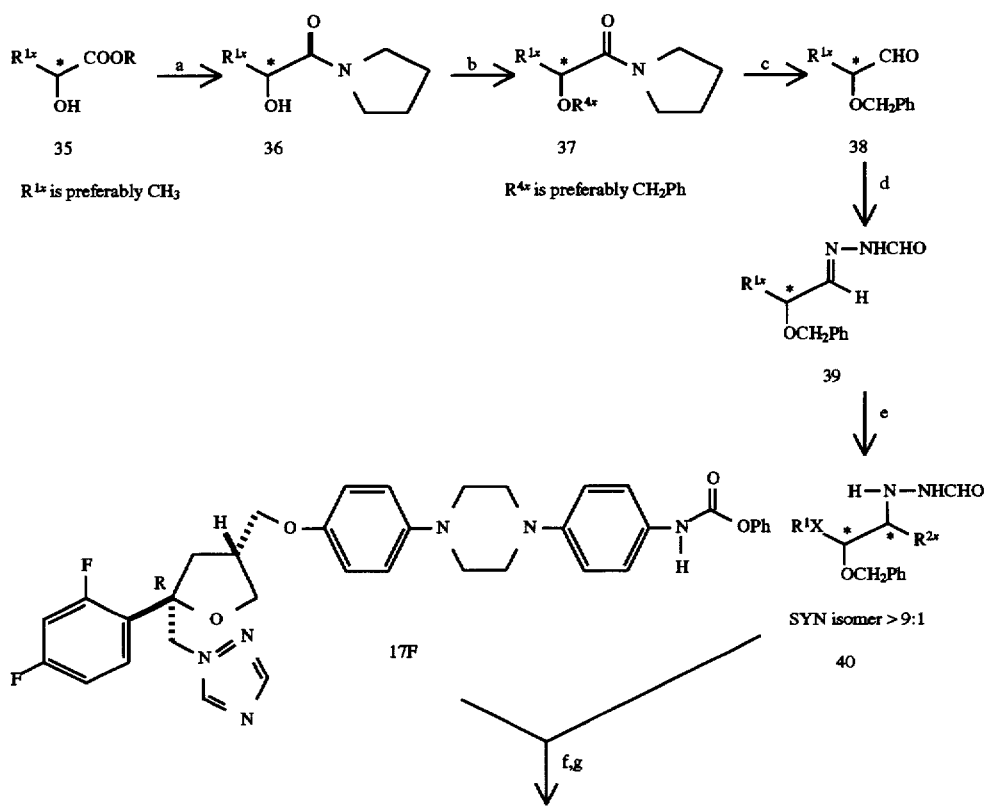

-continued
SCHEME VI
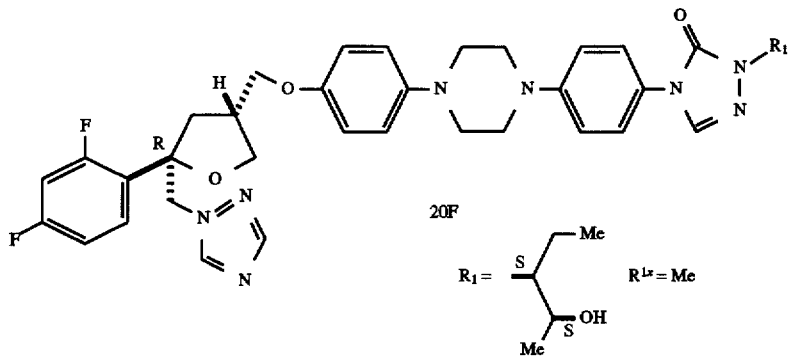
20F
(a) pyrrolidine, r.t., 24 h; (b) R$^{4x}$—X, NaH, DMF; (c) RED-AL, toluene. -20°;
(d) H$_2$NNHCHO, MeOH; (e) R$^{2x}$MgBr, Et$_2$O, -10° C. to r.t., 24 h; (f) 17F of
Scheme V and procedure of Example 32d; (g) H$_2$, Pd, HCOOH, 80° C.
Scheme VII
Preparation of Polyether Esters
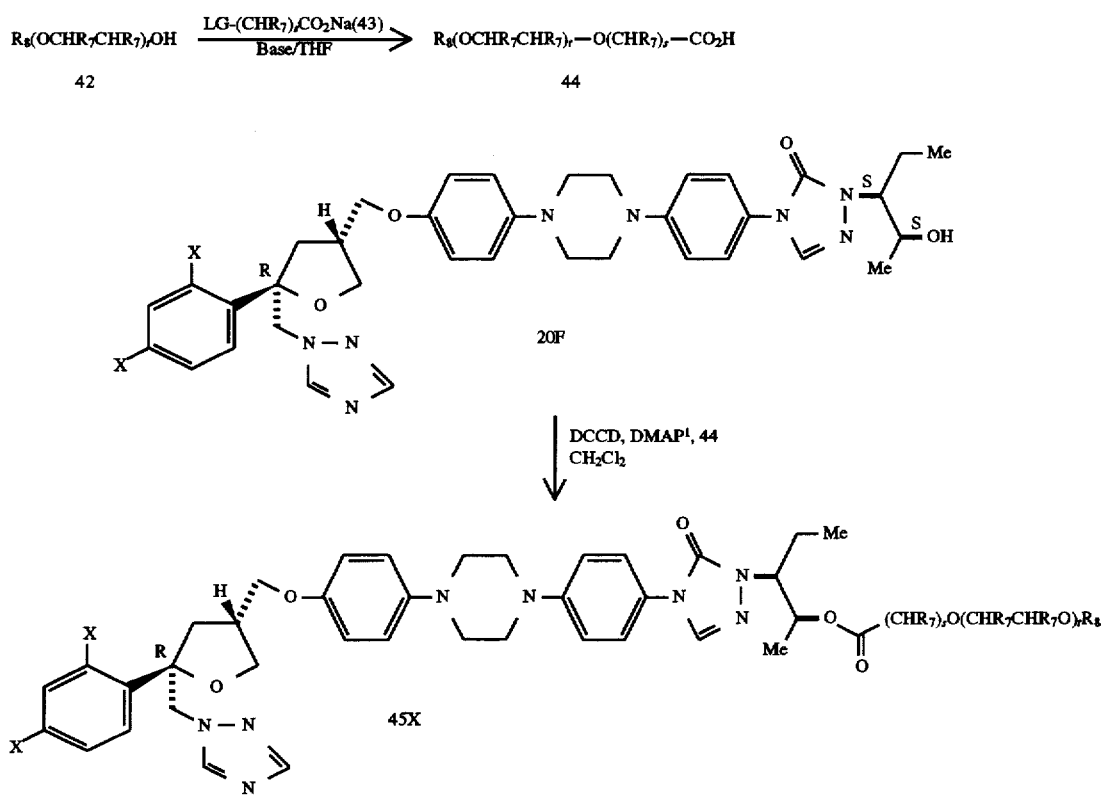
1 DCCD = Dicyclohexylcarbodiamide
DMAP = 4-(N,N-Dimethylamino)Pyridine TABLE for Scheme VII using 20F (X = F) $R^1 =$ [structure with S, Me, OH]

| 42 | 43 | 45 X | M.S. M+ |
|---|---|---|---|
| — | PGOCH$_2$CO$_2$H PG = Protecting Group, e.g., CH$_2$Ph | COCH$_2$OH | 759.3 |
| CH$_3$(OCH$_2$CH$_2$)$_3$OH | ClCH$_2$CO$_2$H | COCH$_2$O(CH$_2$CH$_2$O)$_3$Me | 905 |
| CH$_3$(OCH$_2$CH$_2$)$_3$OH | ClCH$_2$CO$_2$Na | —COCH$_2$O(CH$_2$C$_2$O)Me | 817 |
| CH$_3$(OCH$_2$CH)$_2$OH | ClCH$_2$CO$_2$Na | —COCH$_2$O(CH$_2$CH$_2$O)$_2$Me | 861 |
| CH$_3$(OCH$_2$CH$_2$)$_3$OH | ClCH$_2$CO$_2$Na | —COCH$_2$O(CH$_2$CH$_2$O)$_3$Me | 903 |
| HO$_2$C(OCH$_2$CH$_2$)$_2$OH | ClCH$_2$CO$_2$Na | —COCH$_2$O(CH$_2$CH$_2$O)$_2$CO$_2$H | 905 |
| PEG2000 | ClCH$_2$CO$_2$Na | —COCH$_2$OPEG2000 | a |
| PEG5000 | ClCH$_2$CO$_2$Na | —COCH$_2$OPEG5000 | a |

<sup>a</sup>A range in MS values were observed which corresponded to the molecular weight range of the PEG2000 and PEG5000 used as starting materials.

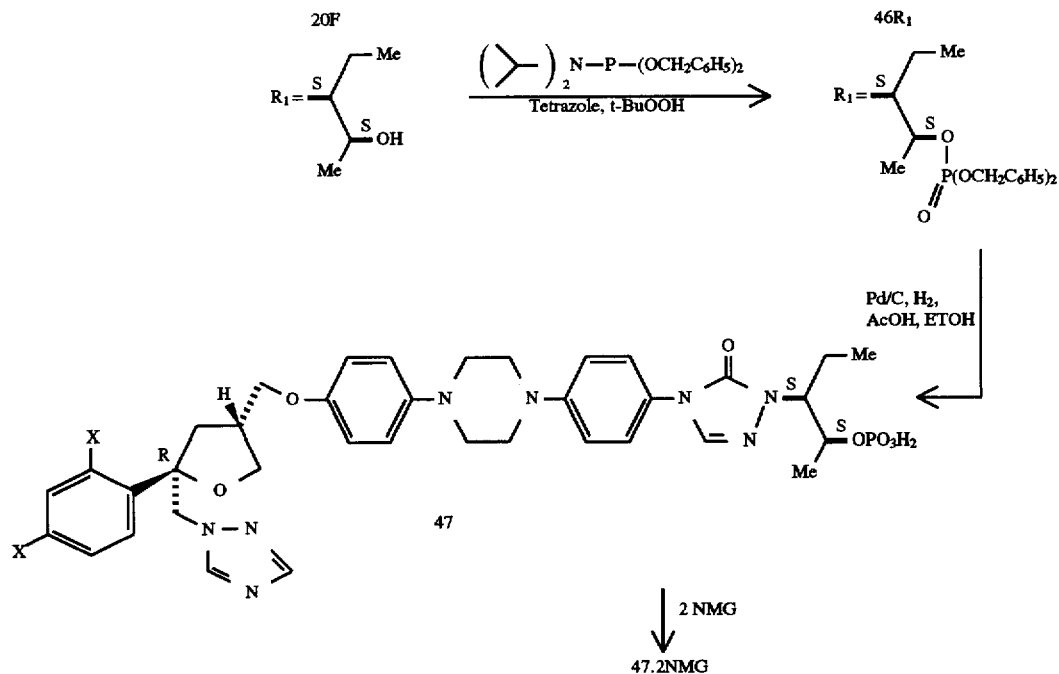

Phosphate Esters
Scheme VIIIA

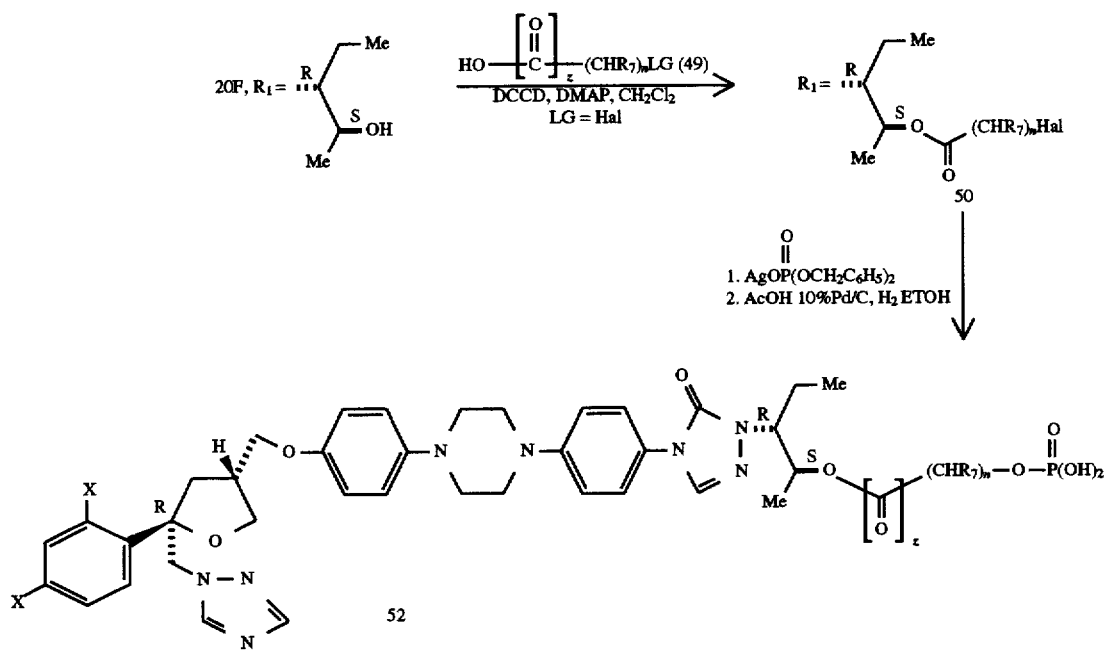

SCHEME VIIIB

| TABLE for Scheme VIIIA | |
|---|---|
| X = F | |
| 47 R¹ | M.S. (M⁺) |
| S-CH(Me)-CH(Me)-OPO₃H₂ .2NMG | 781.8 |
| S-CH(Me)-CH(Me)-OPO₃H₂ .2NMG | 781.7 |
| S-CH(Me)-CH(Me)-OP(OH)-OC₆H₄OH (O) | 873.3 |
| R-CH(Me)-CH(Me)-OP(OCH₂C₆H₅)₂ (O) | 961.4 |
| S-CH(Me)-CH(Me)-OP(OCH₂C₆H₅)₂ (O) | 961.2 |

| TABLE for Scheme VIIIB | | |
|---|---|---|
| 49 | 52R₁ | M.S. (M⁺) |
| HOCOCH₂Cl | S-CH(Me)-CH(Me)-OCOCH₂OPO₃H₂ .2NMG | 839 |
| HOCO(CH₂)₄OH | R-CH(Me)-CH(Me)-OCO(CH₂)₄OPO₃H₂ .2NMG | 881.3 |
| HOCO(CH₂)₄OH | S-CH(Me)-CH(Me)-OCO(CH₂)₄OPO₃H₂ .2NMG | 881.3 |
| S—HOCOCH(.OH)CH₃ * | R-CH(Me)-CH(Me)-OCO-C(OPO₃H₂)(H)(CH₃) .2NMG | 853.2 |

5,703,079
Scheme VIIIC
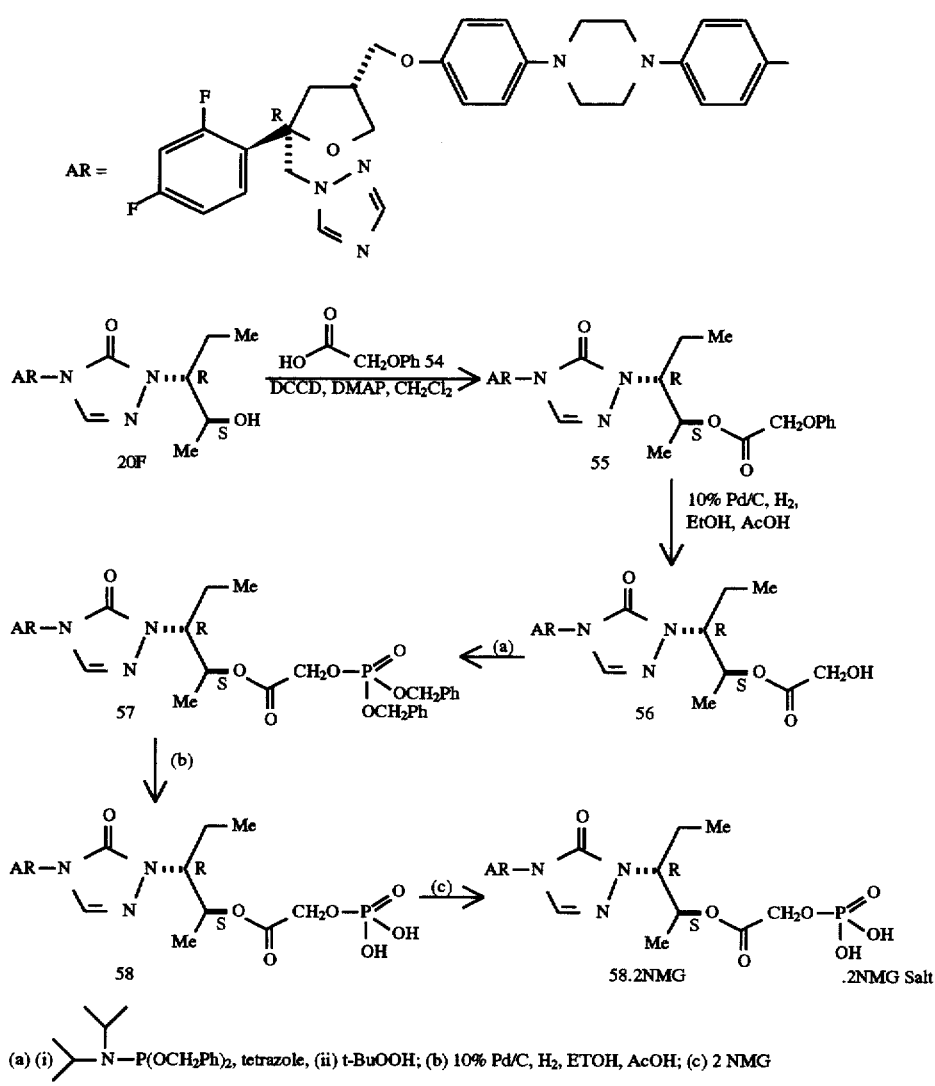
(a) (i) iPr₂N—P(OCH₂Ph)₂, tetrazole, (ii) t-BuOOH; (b) 10% Pd/C, H₂, ETOH, AcOH; (c) 2 NMG
TABLE for Scheme VIIIC
| 54a | 58 R₁ | M.S. (M⁺) |
|---|---|---|
| o-(HO₂CCH₂C₆H₄OCH₂Ph) | (structure shown) | 929.2 |

TABLE for Scheme VIIIC-continued
| 54a | 58 R₁ | M.S. (M⁺) |
|---|---|---|
| o-(HO₂C(CH₂)₂C₆H₄OCH₂Ph | (structure with —Me, S, Me, O, linked to phenyl-O-P(=O)(OH)(OH)·2NMG) | 929.9 |
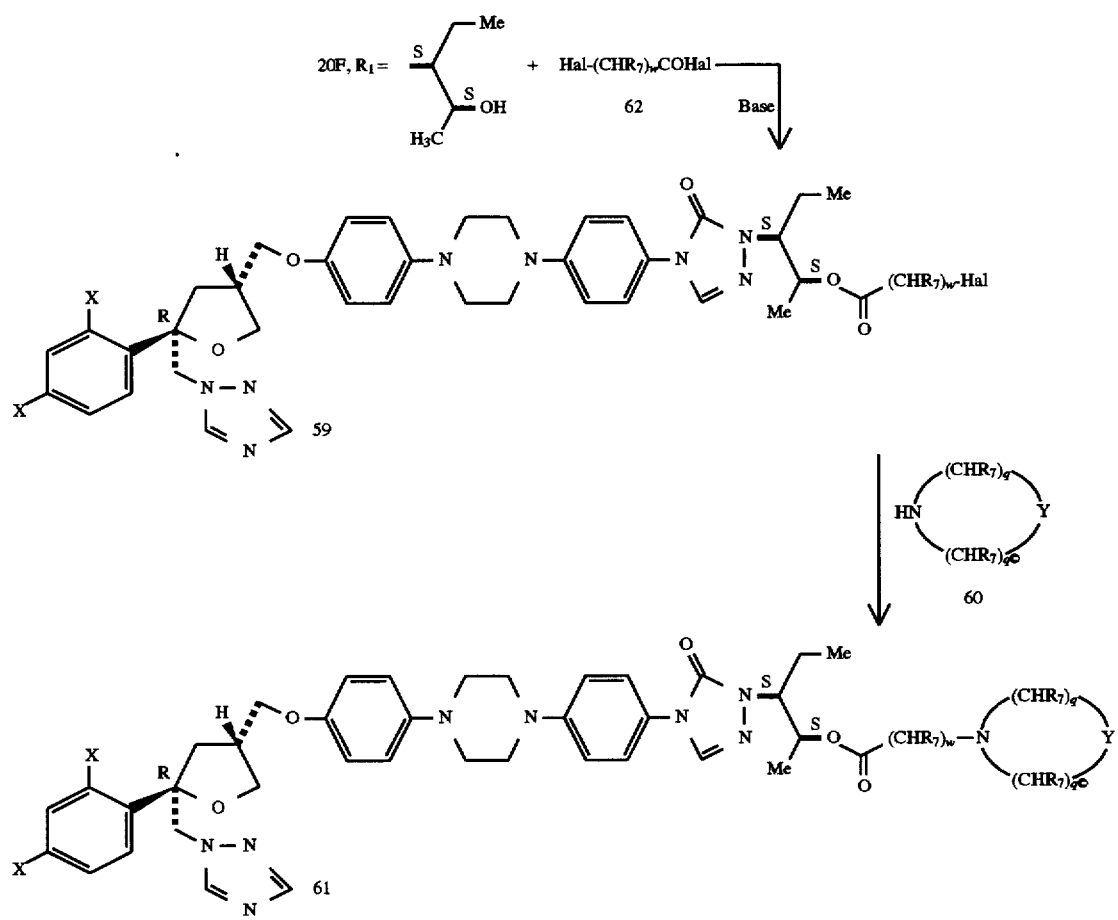
Scheme IX
Preparation of Heterocyclic Esters
TABLE for Scheme IX
| 61 R₁ | M.S. (M⁺) |
|---|---|
| (structure: S—Me, Me, S-OCOCH₂-N-morpholine) | 828 |
TABLE for Scheme IX-continued
| 61 R₁ | M.S. (M⁺) |
|---|---|
| (structure: S—Me, Me, S-OCOCH₂-N-piperazine-NMe) | 841 |

TABLE for Scheme IX-continued
| 61 R$_1$ | M.S. (M$^+$) |
|---|---|
| (structure: -CH(Me)S-CH(Me)S-OCOCH$_2$-N-piperidine) | 826 |
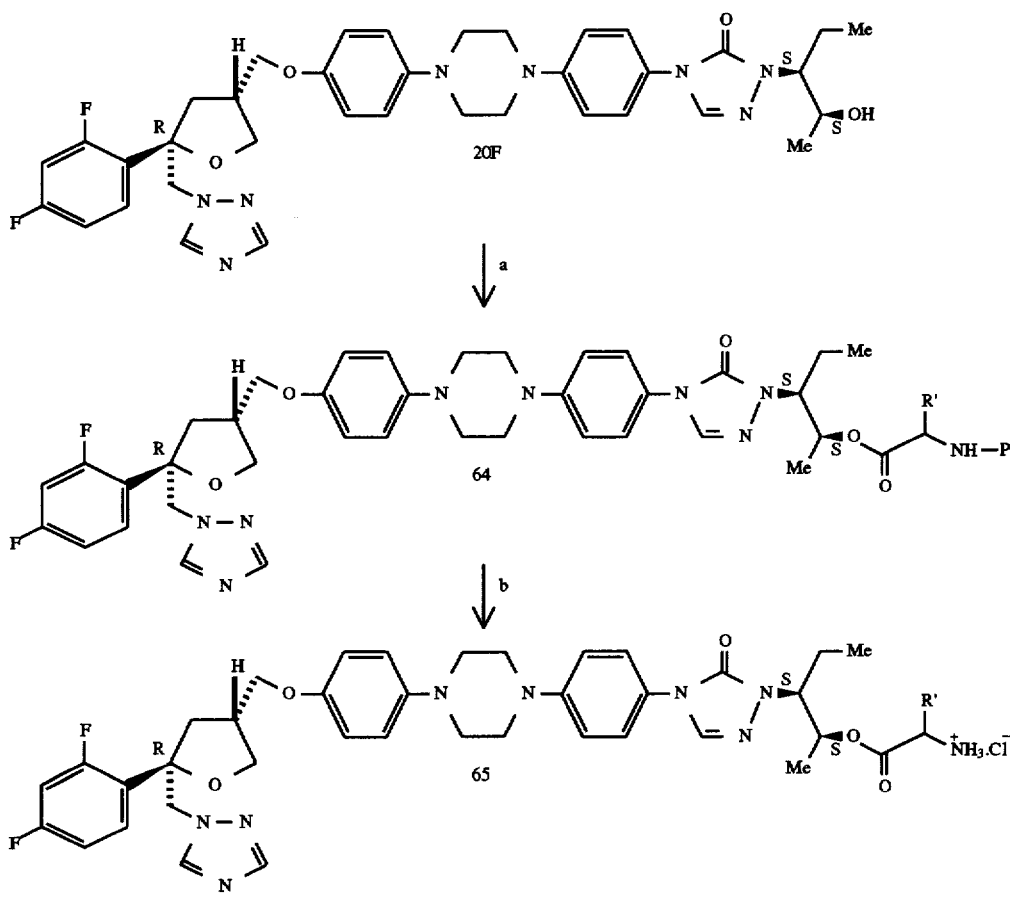
SCHEME X
Reagents: (a) R'—CH(NH.P)—COOH, DCCD, CMAP, CH$_2$Cl$_2$; (b) HCl in dioxane
Where R' = CH$_3$, C$_2$H$_5$, H; R$_2$ = H, CH$_3$, CH$_2$OH, CH(OH)CH$_3$, CH$_2$SH, CH$_2$CONH$_2$, CH$_2$CH$_2$CONH$_2$, CH(CH$_3$)$_2$, CH(CH$_3$)CH$_2$CH$_3$, CH$_2$CH$_2$SMe, CH$_2$COO$^-$,
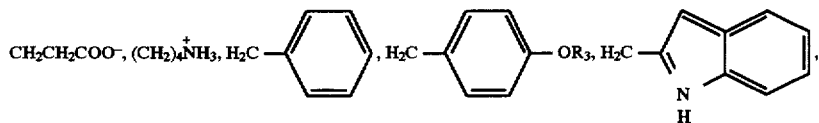
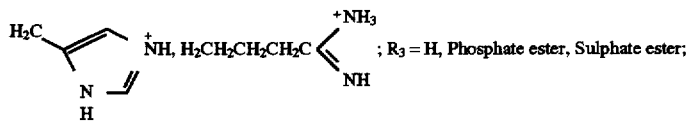
; R$_3$ = H, Phosphate ester, Sulphate ester;

-continued
SCHEME X
and P = N-tert-butoxycarbonyl (N-t-Boc), or N-Carbobenzyloxy (N-Cbz)
SCHEME XIA
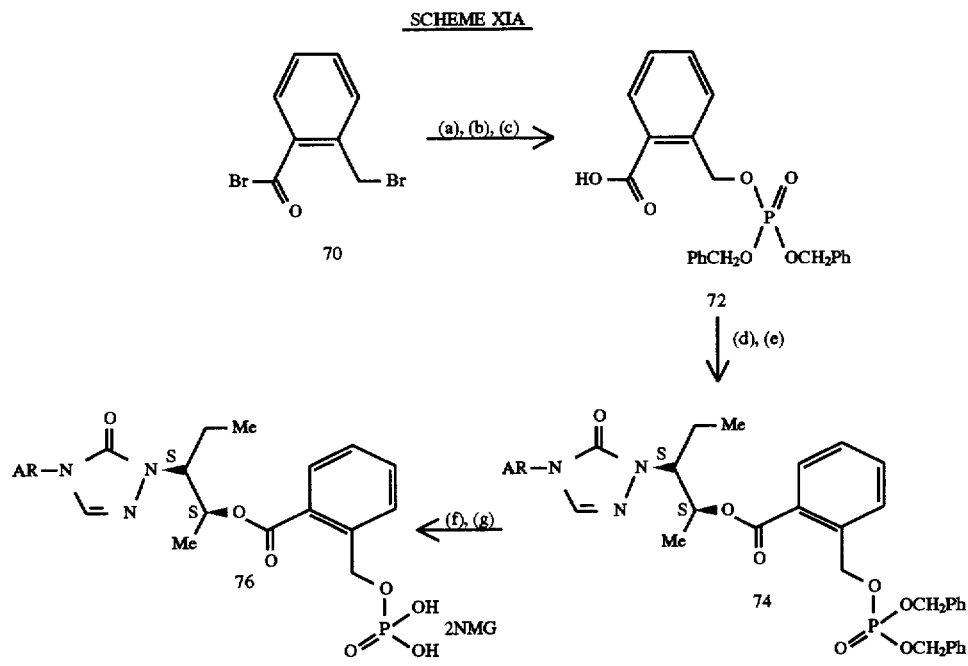
Reagents: (a) 2,2,2-trichloroethanol; (b) silver dibenzyl phosphate; (c) Zn, HOAc-THF;
(d) SOCl₂; (e) 20F, R₁ = 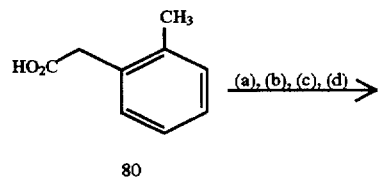 ; (f) H₂, 10% Pd-C; (g) 2eq. N-methyl glucamine.
SCHEME XIB -continued
SCHEME XIB

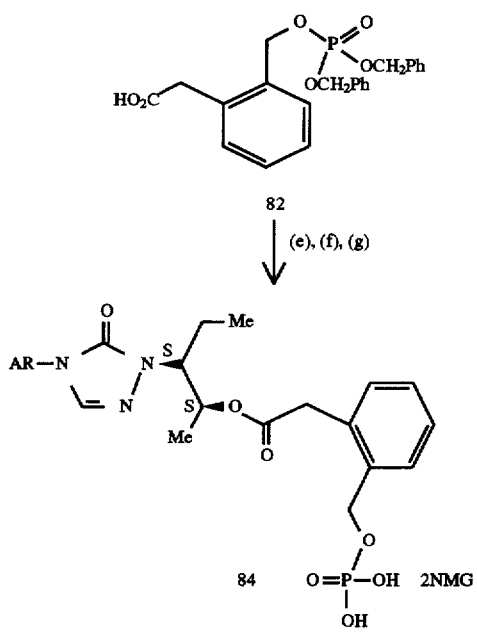

Reagents: (a) 2,2,2-trichloroethanol, DCCD, DMAP;

(b) N-bromosuccinimide; (c) silver dibenzyl phosphate;

(d) Zn, HOAc-THF; (e) 20F, 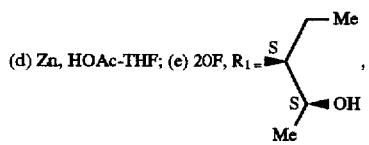

DCCD, DMAP; (f), H$_2$, 10% Pd-C; (g) 2eq. N-methyl glucamine

Scheme IV provides an additional reaction sequence to obtain the compounds of the present invention. Compound 27 is prepared from the methyl ether of compound 12 in Scheme II by subjecting the methyl ether of 12 to the reactions of steps a to g of Scheme II. Reaction of compound 27 with aqueous HBr or BBr$_3$ gives phenolic compound 28. Reaction of compound 28 with one equivalent of NaH and subsequent treatment with, for example, 2-(trimethyl)-silylethoxymethyl chloride ("SEM-Cl")and DMF at ambient temperatures produces SEM-protected compound 29. Deprotonation of compound 29 with NaH followed by reaction of the so-formed anion with tosylate 11 in DMF or DMSO at elevated temperatures produces compound 30. The nitrogen protecting group of 30, e.g., SEM is removed by treatment with, for example, 6NHCl in methanol at ambient temperatures for 3 hr to produce compound 19. Compound 19 is treated with NaH and DMSO at 20° C. for ¾ hr. and thereafter alkylated with R$_1$X to produce compound I. In R$_1$X, R$_1$ is a C3–C8 alkyl group having at least one protected hydroxy moiety, e.g., O-SEM and X' is a leaving group, for example, brosylate. Removal of the hydroxy protecting group from compound 31, e.g., O-SEM is accomplished by, for example, 6NHCl in methanol to give compounds of this invention of formula I.

Scheme V provides a preferred route for preparation of the compounds of this invention set forth in Scheme II. The sodium salt of compound 31 prepared by reaction of (4-[4-(4-nitrophenyl)-1-piperazinyl]phenol with NaH in anhydrous DMSO at 50°–60° C. for 30 minutes is reacted with the 2,4-diflurophenyl tosylate 11F (compound 11 in Scheme II wherein X=F) for 1 h. at 50°–70° C. to provide, after flash silica chromatography or crystallization, compound 15F (compound 15 in Scheme II wherein X=F). Reduction of 15F by hydrogenation in the presence of 5% Pd/C in ethanol containing 1NHCl provided amino compound 16F (compound 16 in Scheme II wherein X=F). Reaction of 16F with phenylchloroformate in anhydrous pyridine at 0°–5° C. for 2h. provided phenylcarbamate 17F (compound 17 of Scheme II wherein X=F). Reaction of 17F with hydrazine hydrate in 1,2-dimethoxyethane at 80° C. for 4 h. provided the semicarbazide 18F (compound 18 of Scheme II wherein X=F). Reaction of 18F with formamidine acetate and Et$_3$N in 2-methoxyethanol under dry argon in stirred reactor at 80° C. overnight provided 3H-1,2,4-triazol-3-one 19F (compound 19 in Scheme II wherein X=F). Reaction of compound 19(f) with R$_1$X in accordance with the procedure of Scheme IV produced compounds of formula I.

Scheme VI provides an alternative, stereoselective route for preparation of the preferred compounds of this invention. Compound 35 (e.g. S-lactic acid methylester) is contacted with excess pyrrolidine in methylene chloride for 24 hours at room temperature to give amide 36. Reaction of 36 and NaH with for example, benzyl halide in DMF gave 37. Selective reduction of amide 37 with a 3.4M solution of sodium bis(2-methoxyethoxy)aluminum hydride ("RED-Al") in toluene at −20° C. gave aldehyde 38. Reaction of aldehyde 38 with H$_2$NNHCHO in methanol gave 39 which was reacted with a Grignard reagent e.g. ethylmagnesium bromide in dry ether at a temperature of −10° C. to room temperature for 24 hours to give 40 wherein the ratio of the S,S isomer: S,R isomer was 94:6. When the Grigand reaction was done in the presence of 1.2 equivalents of bis (trimethylsilyl)acetamide the SS to SR ratio was 99:1. Compound 40 was reacted with compound 17F of Scheme V in toluene in the presence of DBU (1,8-diazabicyclo [5.4.0]undec-7-ene) for six hours at 80° C. Cyclization was effected by raising the temperature to 100°–110° C. and continuing to maintain this temperature overnight. After purification via TLC, 20F was obtained. Treatment of 20F with hydrogen and palladium black in methanol containing formic acid heated to 60° C. gave the crude product which was isolated and purified (via TLC) to give compound 20F i.e. the compound of formula III wherein

R$_5$=

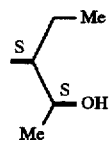

and X=F, Mt=701*

The reaction of the Grignard reagent on the propanimine 39 produces 40 wherein the absolute stereochemistry induced at the new chiral center in 40 is substantially the same (i.e., S) as that at the chiral carbon in 39. By the term "substantially the same" as used herein is meant the ratio of S:S to S:R (in e.g., 40) is greater than 9:1, preferably is greater than 15:1 and most preferably is at least 99:1.

The mass spectral data presented herein as M+ are parent ions which were determined by Fast Atom Bombardonment (FAB) technique and represent the [M+H$^+$], i.e. {molecular ion+1} peaks.

We consider that Schemes I–VI set forth the preferred processes to prepare the alcohol compounds of this invention. Other processes for preparing the alcohol compounds of this invention are disclosed in commonly-assigned U.S. patent application Ser. No. 08/425,129, filed Apr. 19, 1995 and Ser. No. (Attorney's Docket No. CD0475) filed Apr. 19, 1995; and these two patent applications are hereby incorporated by reference.

Scheme VII provides a general method for preparation of the polyether esters of alcohols of the present invention. The alcoholate of alcohol ether 42 e.g. $CH_3(OCH_2CH_2)_3OH$ i.e., 42 wherein $R_7$=H and t=3, was prepared by reaction, of 42 with excess strong base e.g. NaH in an anhydrous ether e.g. THF at ice bath temperatures. The so-formed reaction mixture was stirred for several hours i.e., 2 or more and the sodium salt of acid 43 e.g. sodium salt of chloroacetic acid (43 wherein LG=Cl, $R_7$=H and s=1) was added thereto. The so-formed reaction mixture was stirred at ice-bath temperatures and stirring was continued as temperature was allowed to warm to room temperature. Water was carefully added to the reaction mixture and the polyether acid 44 was separated and purified by conventional techniques.

To a solution of 44 in $CH_2Cl_2$ was added 1.3–1.5 equivalents of the base 4-(N,N-dimethylamino)pyridine ("DMAP") and 20F wherein $R_1$=

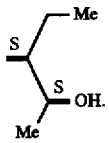

The temperature of the so formed reaction mixture was lowered by use of an ice bath and 1.3–1.5 equivalents of dicyclohexylcarbodiimide ("DCCD") was added thereto. The so-formed reaction mixture was continuously stirred as the temperature was allowed to warm to room temperature. The dicyclohexyl urea precipitate was removed and the crude product isolated by conventional techniques. The so formed residue was purified by chromatography on silica gel to provide the pure compound [M+H]$^+$=906 by FAB. By the appropriate substitution of different starting materials 42 and 43 the compounds 45 listed in Table for Scheme VII were prepared. The MS values for products listed under 45 in the Table for Scheme VII were measured by Fast Atom Bombardment ("FAB").

Schemes VIII A–C illustrate the generalised methods for preparing phosphate esters of the alcohols of this invention. Scheme VIIIA provides a method for preparation of phosphate esters of formula IV wherein $R_6$ is

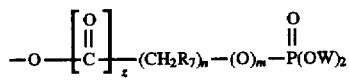

and z=m=n=0. Compound 20F of Scheme II in methylene chloride at room temperature was reacted with 1.5 equivalents of N,N-diisopropyl-dibenzylphosphoramide, and 3 equivalents of a base such as tetrazole, followed by 1.5 equivalents of tert-butyl peroxide (3M in iso-octane) for several hours. The progress of the reaction was followed by TLC (5% methanol:EtOAc v:v) on silica gel. The crude product in EtOAc was washed with sodium thiosulfate and purified using standard techniques to provide the dibenzylphosphate ester 46. The dibenzyl ester groups of 46 were removed to give 47 by treatment of 46 dissolved in equal volumes of ethanol and glacial acetic acid in the presence of 10% Pd/C under a hydrogen atmosphere at room temperature in a stirred reactor overnight. The reaction was continued until no starting material was found by TLC (or NMR).

The catalyst was removed by filtration and the crude phosphate ester 47 was purified by standard techniques. Treatment of 47 in methanol at room temperature with two equivalents of base e.g. NMG (or $Et_3N$) provided 47•2NMG. The compounds 46 and 47 prepared in accordance with Scheme VIIIA are listed in the Table for Scheme VIIA.

Scheme VIIIB illustrates preparation of phosphate esters of formula IV wherein $R_6$=

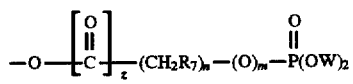

z=m=1 and n=o. Compound 20F dissolved in methylene chloride was treated with 1.3 equivalents of DMAD 1.3 equivalents of DCCD and 1.3 equivalents of the acid 49 of the formula

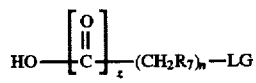

e.g., $HO_2C(CH_2)_4Br$, i.e., z=1, n=4, $R_7$=H and the leaving group LG is Br. The reaction was stirred at room temperature until no starting material was found by TLC purification of the crude product gave bromide 50, a white solid wherein

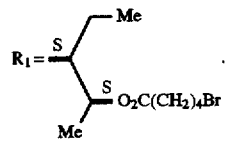

The bromide 50 in benzene was heated at 80° C. overnight with 1.5 equivalents of silver dibenzylphosphate (available from Sigma Chemical Co., St. Louis). The reaction mixture was cooled and washed with aqueous base, e.g., $K_2CO_3$. The crude product was separated and purified by silica gel column chromatography to give the dibenzyl phosphate ester 51. Treatment of 51 in ethanol/glacial acetic acid with 10% Pd/C under a hydrogen atmosphere overnight at room temperature gave phosphate ester 52. Treatment of 52 in methanol with two equivalents of base e.g. NMG (or $Et_3N$) gave 52•2NMG.

Scheme VIIIC provides an alternative procedure for preparation of phosphate esters of formula IV wherein Re is as defined above for Scheme VIIIB and z=1 and n=1. The benzyl ether of methyl acetate 53 in methanol-water and excess base e.g. $K_2CO_3$ were stirred overnight at room temperature to give the benzyl ether 54. Reaction of a solution of 20F and 54 in methylene chloride with a 1.3–1.5 equivalents of DCCD and DMAP at room temperature overnight gave ester 55. The benzyl ether group of 55 was removed by treatment with excess 10% Pd/C in ethanolglacial acid under a hydrogen atmosphere at room temperature overnight. Purification of the crude product gave 56. Treatment of 56 with 1.5 equivalents of $N_1N$-diisopropyldibenzylphosphoramide and 3 equivalents of tetrazole and followed by 1.5 equivalents of tert-butyl peroxide in accordance with the procedure of Scheme VIIIB gave dibenzyl ester 57. Removal of the dibenzyl groups with 10% Pd/C in ethanol-glacial acetic acid under hydrogen atmosphere gave (as described hereinabove) phosphate ester 58. Treatment of 58 with two equivalents of base, e.g. NMG, gave 58•2NMG.

Additional phosphate esters of this invention of the formula

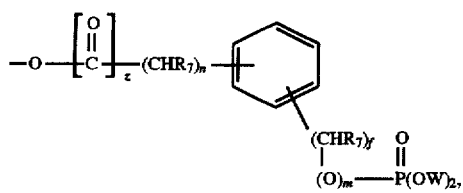

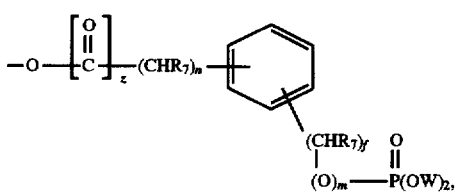

wherein z=m=1, n=1 or 2, f=0 or 1, and W=H, such as listed in the Table for Scheme VIIIC are prepared from compound 20F wherein $R_1$ is the same as that used in Scheme VIIIA by substituting equivalent amounts of starting materials 54a and 54b for compound 54 and thereafter following the procedures shown in Scheme VIIIC.

Scheme IX illustrates the preparation of heterocyclic esters of the present invention. Compound 20F, wherein

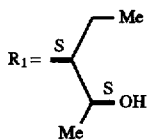

dissolved in methylene chloride is reacted with compound 62 in the (Hal=Br or Cl, w=1–5, e.g., Cl—$CH_2$—COCl) in presence of a base such as pyridine at a temperature of 0°–5° C. for four hours. The reaction was placed in a refrigerator overnight. Additional compound 62 and base could be added, if necessary, and the reaction continued until no 20F is present by TLC. Purification of the crude product by column chromatography on silica gel gave pure 59 (w=1, Hal=Cl). Reaction of 59 with excess of the nitrogen heterocyclic compound 60 (e.g., Y=NH, $R_7$=H and q=4) at a temperature of 50°–60° C. for 1 hour produced 61. Substitution of nitrogen heterocyclic compound 60 with a five and six membered compounds, e.g. morpholine, N-methylpiperidine provided the compounds listed in Table below Scheme IX.

Scheme X illustrates preparation of the amino acid ester derivatives of the compounds of this invention. Compound 20F is contacted with excess N-(-butoxy carbonyl α-amino acid or α-amino alkanoate in the presence of DCCD and DMAP in an aprotic solvent such as $CH_2Cl_2$ at 0° C. to 25° C. The reaction is followed by TLC and additional α-amino acid and DCCD are added, if necessary, to insure the starting material 20F is completely converted into amino acid ester derivative 64. Compound 64 is treated HCl in dioxane to provide the α-amino acid ester as the acid addition salt 65. Purification of the crude products is accomplished by standard techniques. When carbobenzoxy is used as the protecting group, hydrogen over palladium black is used to remove the protecting group in step b. Other protecting groups may be used such as those disclosed in "Protective Groups in Organic Synthesis" by T. W. Green and P. G. M. Wuts. John Wiley and Sons 1991 NY at pages 97–98 or 389–394.

Schemes XIA and XIB illustrate the preparation of additional phosphate esters of this invention of the formula wherein z=f=m=1, n=0 or 1. and W=H.

In Scheme XIA, the benzoyl bromide 70 is treated with 2, 2, 2-trichloroethanol to produce the corresponding trichloroethyl ester. Treatment of the trichloroethyl ester with excess silver dibenzyl phosphate under conditions similar to those used in Scheme VIIIC converted the benzyl bromide into a dibenzyl phosphate ester Removal of the trichloroethyl ester group was accomplished by use of zinc in acetic acid-THF to give the dibenzyl phosphate ester 72. Treatment of 72 with thionyl chloride gave the corresponding acid chloride which was contacted with a solution of 20F in methylene chloride under conditions of step one in Scheme VIIIC to give ester 74. Removal of the dibenzyl ester groups of 74 with 10% Pd/C under a hydrogen atmosphere as described in Scheme VIIIA produced the corresponding phosphate ester which was treated with two equivalents of base e.g. NMG to provide 76. In Scheme XIB, the 2-methylphenylacetic acid 80 was esterified with 2, 2, 2-trichloroethanol and the so-formed ester was converted into corresponding the benzyl bromide by treatment with N-bromosuccinimide. The treatment of the benzyl bromide with excess silver dibenzyl phosphate under conditions of Scheme VIIIC provided the corresponding dibenzyl phosphate ester. Removal of the trichloroethyl ester group was accomplished with zinc in acetic acid-THF to give dibenzyl phosphate 82. Treatment of a solution of 82 and 20F (wherein $R_1$ is the same as in Scheme VIIIA) with DCCD and DMAP provided the corresponding phosphate ester. Treatment of the phosphate ester with two equivalents of NMG gave compound 84.

The alkanoate and alkenoate esters of 20F are conveniently prepared by standard synthetic techniques, (for example, by reaction of the anhydride or acid halide of the alkanoic acid or alkenoic acid in tghe presence of base e.g. pyridine) produced the alkanoate or alkenoates of the compounds of formula I.

The sulfate esters may be prepared by reaction of the alcohol compounds of formulas I to IV with sulfur trioxide in the presence of excess pryridine at temperatures of 70°–90° C. for at least 2 hours in accordance with the procedure of R. M. Moriarty et. al. Tetrahedron Letters, Vol. 35, No. 44, p 8103–8106 (1994).

The compounds of formula I may also be prepared by reaction of compound 11 with alcohols of formula HOY in the presence of a strong base, e.g., NaH in an aprotic solvent, such as DMSO.

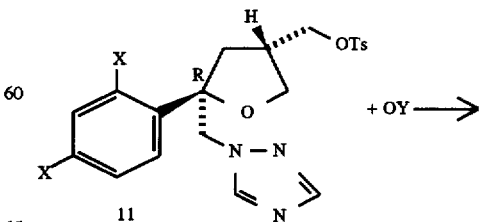

(R)-"Tosylate" Series

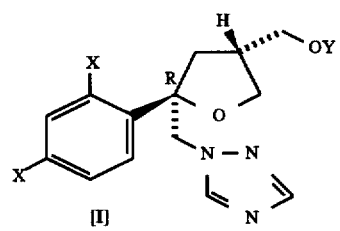

See Example 15
wherein X=F or Cl

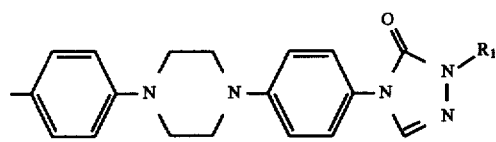

and R$_1$=a (C$_3$-C$_8$) alkyl group substituted by one or two hydroxy moieties.

Compounds represented by formula I exhibit broad spectrum antifungal activity, in conventional antifungal screening tests, against human and animal pathogens, such as the following: Aspergillus, Blastomyces, Candida, Cryptococcus, Coccidioides, Epidermophyton, Fonsecaea, Fusarium, Mucor, Saccharomyces, Torulopsis, Trichophyton, Trichosporon, Sporothrix and Pneumocysitis.

The preferred compounds of formula IV exhibit topical, oral and parenteral antifungal activity in vivo tests in animals and such activity is unexpectedly better than that of existing antifungal agents e.g. itraconazole and fluconazole as well as that of the azole compounds specifically disclosed by Saksena et al. in U.S. Pat. No. 5,039,676 and International Publication No. WO 93/09114.

The antifungal compounds of formula I and pharmaceutical compositions of this invention are expected to exhibit anti-allergic, anti-inflammatory and immunomodulating activities, broad spectrum antiinfective activity, e.g., antibacterial, anti-protozoal and antihelminthic activities.

The present invention also provides a composition for treating or preventing fungal infections comprising an antifungally effective amount of a compound represented by formula I or a pharmaceutically acceptable salt thereof and a pharmaceutically acceptable carrier or diluent therefor.

The pharmaceutical compositions of the present invention may also contain a fungicidally effective amount of other antifungal compounds such as cell wall active compound. The term "cell wall active compound", as used herein, means any compound that interferes with the fungal cell wall and includes, but is not limited to, compounds such as papulacandins, echinocandins, and aculeacins as well as fungal cell wall inhibitors such as nikkomycins, e.g, nikkomycin K and others which are described in U.S. Pat. No. 5,006,513 which is hereby incorporated by reference.

The pharmaceutically acceptable salts of the compounds of the present invention include pharmaceutically acceptable acid and base addition salts.

The preferred pharmaceutically acceptable acid addition salts are nontoxic acid addition salts formed by adding to the compounds of the present invention about a calculated amount of a mineral acid, such as HCl, HBr, H$_2$SO$_4$, HNO$_3$ or H$_3$PO$_4$, or of an organic acid, such as an alkyl or arylsulfonic acid such as methanesulfonic, isithionic, paratoluenesulfonic, naphthylsulfonic and the like.

The pharmaceutically acceptable bases found suitable for use in the present invention are those which form pharmaceutically acceptable salts of the acidic pharmaceutically acceptable esters of the antifungal compounds of formulas I, II, III or IV and include suitable organic and inorganic bases. Suitable organic bases include primary, secondary and tertiary alkyl amines, alkanolamines, aromatic amines, alkylaromatic amines and cyclic amines. Exemplary organic amines include the pharmaceutically acceptable bases selected form chloroprocaine, procaine, piperazine, glucamine, N-methylglucamine, N-N-dimethyl glucamine ethylendediamine, diethanolamine, diisopropylamine, diethylamine, N-benzylenediamine, diethanolamine, diisopropylamine, diethylamine, N-benzyl-2-phenylethylamine, N-n'dibenzylethylenediamine, choline, clemizole, triethylamine ("ET$_3$N"), tris(hydroxymethyl) aminomethane, or D-glucosamine. The preferred organic bases include N-methyl glucamine ("NMG"), diethanolamine, and tris(hydroxymethyl) aminomethane ("TRIS"). Use of two equivalents of NMG in this invention is more preferred. The suitable inorganic bases also include alkali metal hydroxides such as sodium hydroxide.

The pharmaceutical compositions of the present invention may be adapted for any mode of administration e.g., for oral, parenteral, e.g., SC, IM, IV and IP, topical or vaginal administration or by inhalation (orally or intranasally) Such compositions are formulated by combining the compound of formula I or an equivalent amount of a pharmaceutically acceptable salt of compound I with an suitable, inert, pharmaceutically acceptable carrier or diluent.

Examples of suitable compositions include solid or liquid compositions for oral administration such as tablets, capsules, pills, powders, granules, solutions, suppositories, troches, lozenges, suspensions or emulsions. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet, the active compound is mixed with carrier having the necessary binding properties in suitable proportions and compacted in the shape and size desired.

Topical dosage forms may be prepared according to procedures well known in the art, and may contain a variety of ingredients, excipients and additives. The formulations for topical use include ointments, creams, lotions, powders, aerosols, pessaries and sprays.

For preparing suppositories, a low melting wax such as a mixture of fatty acid glycerides or cocoa butter is first melted, and the active ingredients are dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution with an appropriate amount of a hydroxypropyl α- β or -γ-cyclodextrin having 2 to 11 hydroxypropyl groups per molecule of cyclodextrin, polyethylene glycol, e.g., PEG-200 or propylene glycol, which solutions may also contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water. A particularly preferred aqueous pharmaceutical composition may be prepared from the compounds of formulas I to IV together with hydroxypropyl-β-cyclodextrin in water. The use of derivatives of α-, β- and γ-cyclodextrins, for example, hydroxpropyl-β-cyclodextrin are disclosed by N. Bodor U.S. Pat. No. 4,983,586, Pitha U.S. Pat. No. 4,727,064 and Janssen Pharmaceutical International Patent Application No. PCT/EP 84/00417.

The pharmaceutical compositions of the present invention may be prepared by admixing the pharmaceutically acceptable carrier, e.g., a hydroxypropyl-β-cyclodextrin in water, and adding thereto an antifungally effective amount of a drug of the present invention. The solution so formed is filtered, and optionally, the water may be removed by well known methods, e.g., rotatory evaporation or lyophilization. The formation of the solution may take place at a temperature of about 15° to 35° C. The water is normally sterilized water and may also contain pharmaceutically acceptable salts and buffers, e.g., phosphate or citrate as well as preservatives. The molar ratio of the antifungal compound of formula I to hydroxpropyl-β-cyclodextrin is about 1:1 to 1:80, preferably 1:1 to 1:2. Normally the hydroxypropyl-β-cyclodextrin is present in molar excess.

Also included are solid form preparations which are intended to be converted, shortly before use, into liquid form preparations for either oral or parenteral administration. The solid form preparations intended to be converted to liquid form may contain, in addition, to the active materials, such as compounds of this invention, and optionally a cell wall active compound, especially a fungal cell wall inhibitor, e.g., a nikkomycin, flavorants, colorants, stabilizers, buffers, artificial and natural sweeteners, dispersants, thickeners, solubilizing agents and the like. The solvent utilized for preparing the liquid form preparations may be water, isotonic water, ethanol, glycerin, polyethylene glycols, propylene glycol, and the like, as well as mixtures thereof.

Parenteral forms to be injected intravenously, intramuscularly, or subcutaneously are usually in the form of a sterile solution, and may contain salts or glucose to make the solution isotonic.

The topical dosage for humans for antifungal use in the form of a pharmaceutical formulation comprising a compound of formula I (usually in the concentration in the range from about 0.1% to about 20% preferably from about 0.5% to about 10% by weight) together with a non-toxic, pharmaceutically acceptable topical carrier, is applied daily to the affected skin until the condition has improved.

In general, the oral dosage for humans for antifungal use ranges from about 1 mg per kilogram of body weight to about 30 mg per kilogram of body weight per day, in single or divided doses, with about 1 mg per kilogram of body weight to about 20 mg per kilogram of body weight per day being preferred and the dose of about 1 mg per kilogram of body weight to about 10 mg per kilogram of body weight per day being most preferred.

In general, the parenteral dosage for humans for antifungal use ranges from about 0.25 mg per kilogram of body weight per day to about 20 mg kilogram of body weight per day, in single or divided doses, with about 0.5 to about 10 mg per kilogram of body weight per day being preferred.

The exact amount, frequency and period of administration of the compounds of the present invention for antifungal use will vary, of course, depending upon the sex, age and medical condition of the patent as well as the severity of the infection as determined by the attending clinician.

GENERAL EXPERIMENTAL

The compounds of this invention are prepared in accordance with Schemes I–IX hereinabove and the following Examples using commercially available starting materials.

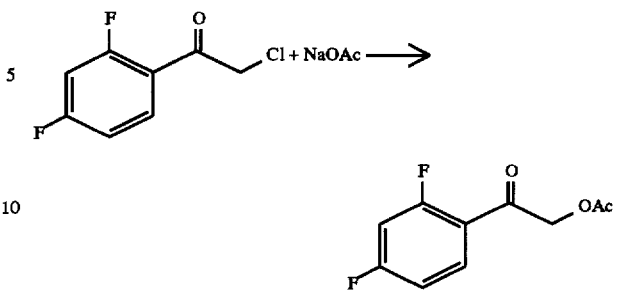

EXAMPLE 1a

2-Acetyloxy-1-(2,4-difluorophenyl)ethanone

Add 191 g of 2-chloro-2',4°-difluoroacetophenone (Aldrich Chemical Co.) to a mixture of 246 g of sodium acetate, 3 g of NaI, and 3 L of DMF. Stir the mixture at 20° C. for 18 hr. then concentrate it to 1 L. Pour the residue into 6 L of cold dilute aqueous HCl and extract with EtOAc. Wash the extract with brine, dry it over anhydrous $Na_2SO_4$, filter the so-formed mixture, and evaporate the filtrate to leave a residue. Chromatograph the residue on silica gel, eluting with $CH_2Cl$-2-hexane to obtain 198 g of the title compound.

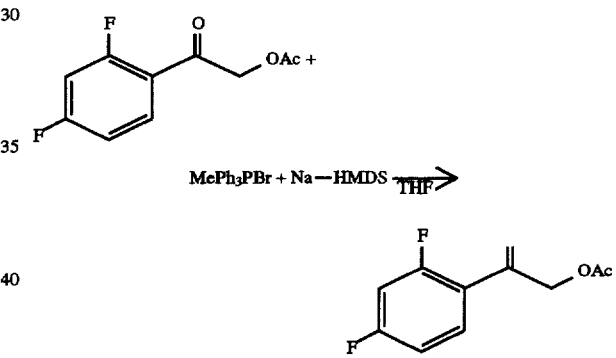

EXAMPLE 1b

1-[2-(2,4-Difluorophenyl)]-2-propenol acetate

Suspend 131 g of $MePh_3PBr$ in 270 mL of mechanically-stirred, dry THF at 20° C. Add 393 mL of 1M $NaN(Me_3Si)_2$ in THF, slowly at first, then rapidly over 5 min. while applying just enough ice cooling to maintain the temperature at <23° C. Stir the so-formed mixture for 1 hr at 20°–24° C., cool it to —70° C., and stir it another ½ hr. Then add thereto a solution of 65.5 g of the product of Example 1a in 140 mL of dry THF, at a rate slow enough to keep the temperature below –70° C. Continue to stir the so-formed reaction mixture in the cold bath overnight during which the temperature rises to 20° C. Add 50 mL of EtOAc to the so-formed suspension, and then add 3 L of hexane. Allow the so-formed mixture to stand for ~15 min., and suction-filter to remove $Ph_3PO$. While the filter cake is still damp, transfer it to a beaker. Triturate the cake thoroughly with ½ L of hexane and suction-filter again to remove the remainder of product. Wash the combined hexane filtrates with 2×1 L of a 1:1 (v/v) MeOH-water, and then with brine. Dry the organic layer over $MgSO_4$, filter and evaporate the filtrate to leave a red oil. Add 1.5 L of hexane and suction-filter through a Celite pad to leave a clear yellow solution. Chromatograph the yellow oil on silica gel, eluting with ½ L of hexane, then 1 L of 15:1 (v/v) hexane-EtOAc. Combine the homogeneous fractions to yield 38.6 g of the title compound as an oil.

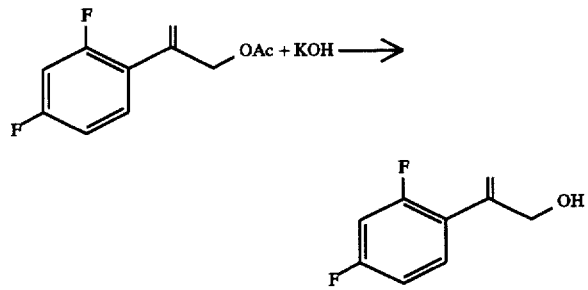

EXAMPLE 1c 2-(2,4-Difluorophenyl)-2-propenol

Dissolve 40 g of the product of Example 1b in 400 mL of dioxane. Add a solution of 18 g of 85% KOH in 315 mL of water. Stir the so-formed mixture vigorously for 1 hr, and then pour the mixture into 1 L of $Et_2O$. Separate the aqueous layer and extract it with 250 mL of $Et_2O$. Combine the organic extracts, and wash them with water and then brine. Dry the organic extract over anhydrous $K_2CO_3$, and add 10 g of charcoal thereto. Filter, and evaporate the filtrate to leave 31.3 g of the title compound as a straw-colored oil.

EXAMPLE 1d (S)-(−)-[2-[2-(2,4-Difluorophenyl)]oxiranyl] methanol

Add 33 g of activated 3 Å molecular sieve powder to a solution of 13 g of L-(+)-diethyl tartarate in 2.3 L of $CH_2Cl_2$, and cool the so-formed mixture to −5° C. Add a solution of 15.4 mL of titanium tetra-isopropoxide in 100 mL of $CH_2Cl_2$ over 2-3 minutes and then cool the so-formed mixture to −22° C. Add 109.5 mL of a 5.5M solution of tert-butylhydroperoxide in 2,2,4-trimethyl-pentane over 4–6 minutes, and cool the so-formed mixture to −25° C. Stir the mixture at −25° C. for 25 minutes and then add a solution of 40 g of 2-(2,4-difluorophenyl)-3-propenol of Example 1c in 100 mL of $CH_2Cl_2$ over 3–4 minutes. Stir the so-formed mixture at −27° C. for 4½ hour. Add 102 mL of 30% aqueous sodium hydroxide saturated with NaCl and stir the so-formed mixture while warming to +10° C. over a ½ hour period. Add thereto 100 g of anhydrous $MgSO_4$ and 33 g of Celite, and stir ½ hour at +10° C. Suction-filter the mixture, wash the so-formed filter cake with 1.2 L of diethyl ether ($Et_2O$) and then 1.5 L of toluene, and dry the combined organic layers over anhydrous $MgSO_4$. Filter the organic layer, and evaporate the filtrate in vacuo to form a residue. Dissolve the residue in 1 L of $Et_2O$ and suction-filter the mixture to remove insolubles. Suction-filter the filtrate through 100 g of silica gel, and wash the pad with 200 mL of fresh $Et_2O$. Evaporate the filtrate in vacuo to give 41 g (94%) of the crude title compound as a yellowish oil, $[\alpha]_D^{25}$ −36.7° (c=1, MeOH); PMR ($CDCl_3$) δ 7.40(m,1H), 6.85(m, 2H), 3.95(m,2H), 3.31(d,1H), 2.84 (d, 1H), 1.91(m,1H, deuterium exchangeable).

EXAMPLE 2

(R)-(+)-[2-[2-(2,4-Difluorophenyl)]oxiranyl] methanol

Follow the procedure of Example 1d, except substitute an equivalent amount of D-(−) diethyl tartarate in place of L-(+) diethyl tartarate to give the crude title compound, $[\alpha]_D^{25}$ +33.9° (c=1, MeOH).

Purify a portion of the crude compound by silica gel chromatography to obtain a sample homogeneous by TLC, $[\alpha]_D^{25}$ +40.0° (c=1, MeOH)

EXAMPLE 3

(R)-(−)-2-(2,4-Difluorophenyl)-3-(1,2,4-triazol-1-yl) -1,2-propanediol

Dissolve 8.91 g of 1H-1,2,4-triazole in 150 mL of anhydrous DMF and cool so-formed mixture to 0°–5° C. Add 2.81 g of sodium hydride (60% oil dispersion) and stir the so-formed mixture 30 minutes at room temperature. Add thereto 10.9 g of the product of Example 1d. Stir the so-formed reaction mixture for 2 hours at 60°–70° C. Cool the mixture to room temperature, add thereto 10 ml of $H_2O$ and evaporate it in vacuo to give a residue. Dissolve the residue in 100 mL of $H_2O$ and 900 ml of ethyl acetate (EtOAc). Extract the $H_2O$ layer with another 250 mL of EtOAc. Wash the combined EtOAc extracts with 100 mL of brine. Dry the EtOAc extracts over anhydrous $MgSO_4$ and evaporate. Triturate the so-formed oily residue with 10 mL of $CH_2Cl_2$ and add 100 mL of $Et_2O$. Stir the $CH_2Cl_2$-$Et_2O$ mixture for 1 hour at room temperature. Filter to give 11.2 g (75%) of the title compound, $[\alpha]_D^{25}$ −70.7 (c=1.0, MeOH), mass spectrum (FAB): 256 [M+H]$^+$. Recrystallize 1.0 g of the filtered product from 5 mL of $CH_3CN$ to give 0.83 g of the title compound, m.p. 99°–100° C.; $[\alpha]_D^{25}$ −71.5° (C=1.0, MeOH); elemental analysis: Calculated for $C_{11}H_{11}F_2N_3O_2 \cdot ½CH_3CN$; 52.27C, 4.57H, 17.78N, 13.78F; Found; 52.26C, 4.58H, 17.54N, 13.78F; PMR(DMSO) δ 8.25 (s,1), 7.66(s,1), 7.33, (m,1), 7.09(t,1), 6.90(t,1), 5.72 (s,1), 5.05(t,1), 4.53(s,2), 3.61(m,2).

EXAMPLE 4

(S)-(+)-2-(2,4-Difluorophenyl)-3-(1,2,4-triazol-1-yl) -1,2-propanediol

Follow the procedure of Example 3, except substitute an equivalent quantity of the product of Example 2 in place of the product of Example 1 to give the title compound; MP. 95°–101° C.; $[\alpha]_D^{25}$+70.0° (c=1.0, MeOH). The PMR and Mass spectra were consistent with the structure of the title compound.

EXAMPLE 5

(R)-2-(2,4-Difluorophenyl)-3-(1,2,4-triazol-1-yl)-1, 2propanediol-1-methanesulfonate Suspend 10.9 g of the powdered product of Example 3 in 150 mL of $CH_2Cl_2$. Add thereto 8.95 mL of triethylamine and cool to the so-formed mixture 0°–5° C. Add 3.64 mL of methanesulfonyl chloride in 20 ml of $CH_2Cl_2$ over 10 min. Stir the so-formed mixture for 1 hour at room temperature. Cool it to 0°–5° C., extract with 100 mL of cold (0°–5° C.) 5% $KH_2PO_4$, followed by 100 mL of cold (0°–5° C.) $H_2O$, followed by 50 mL of brine. Dry the separated organic layer over anhydrous $MgSO_4$ and evaporate to obtain 13.7 g (96%) of the title [M+H+]$^+$; PMR ($CDCl_3$) δ 7.95 (s,1), 7.82 (s,1), 7.53(m,1), 6.81(m,2), 4.84(d,1), 4.65(d,1), 4.46(m,2), 3.05(s,3).

EXAMPLE 6

(S)-2-(2,4-Difluorophenyl)-3-(1,2,4-triazol-1-yl)-1, 2-propanediol-1-methanesulfonate Follow the procedure of Example 5, except substitute an equivalent quantity of the product of Example 4 in place of the product of Example 3 to give the title compound. The PMR is consistent with the structure of the title compound.

EXAMPLE 7

(R)-1-[2-[2-[2,4-Difluorophenyl)]oxiranylmethyl]-1, 2,4-triazole

Dissolve 13.7 g of the product of Example 5 in 200 mL of anhydrous DMF and cool the so-formed solution to 10°–15° C. Add thereto 1.71 g of sodium hydride (60% oil dispersion) and stir the so-formed reaction mixture at room temperature for 90 minutes. Concentrate in vacuo to 50 mL. Add thereto 200 mL of cold $H_2O$ (0°–5° C.) and extract with 3×200 mL portions of EtOAc. Wash the combined EtOAc extracts with 100 mL of brine. Dry the EtOAc extracts over anhydrous $MgSO_4$ and evaporate it to give 10.8 g of a residue. Apply the residue in $CH_2Cl_2$ to a column of 400 g of MPLC grade silican gel previously prepared by slurry packing with $CH_2Cl_2$ containing 1 mL of $Et_3N$ per liter. Elute with 1 liter, each of 25, 50 and 75% EtOAc; $CH_2Cl_2$ (v/v) followed by 2 liters of EtOAc. Combine the fractions to give 6.92 g (68%) of the title compound. Mass spectrum (FAB): 238 [M+H]$^+$; PMR (CDCl$_3$) δ 7.97(s,1), 7.77(s,1), 7.07(m,1), 6.73(m,2); 4.73(d,1), 4.41(d,1), 2.84(d,1), 2.78 (d,1).

EXAMPLE 8

(S)-1-[2-[2-(2,4-difluorophenyl)]oxiranylmethyl]-1, 2,4-triazole

Follow the procedure of Example 7, except substitute an equivalent amount of the product of Example 6 in place of the product of Example 5 to give the title compound. [PMR is consistent with the structure of the title compound].

EXAMPLE 9

Ethyl(5R-cis)-,and (5R-trans)-5-(2,4-Difluorophenyl)-2-oxo-5-[(1H-1,2,4-triazol-1-yl )methyl]tetrahydro-3-furancarboxylate Dissolve 9.35 mL of diethyl malonate in 70 mL of anhydrous DMSO. Add 2.24 g of sodium hydride (60% oil dispersion) in 2 portions and stir the so-formed reaction mixture at room temperature for 1 hour. Add 6.65 g of the product of Example 7 and stir 18 hours at 50°–55° C. Cool to room temperature and pour the reaction mixture into a well-stirred mixture of 500 mL of $KH_2PO_4$, 500 mL of brine, and 1 liter of EtOAc. Separate and extract the $H_2$ layer with another 300 mL of EtOAc. Wash the combined EtOAc extracts with 500 mL of brine, Dry the EtOAc extracts over anhydrous $MgSO_4$ and evaporate to give an oil. Apply the oil with $CH_2Cl_2$ to a column of 400 g MPLC grade silica gel prepared with hexane. Elute with 500 mL of hexane, followed by 2 liters of 50% EtOAc: hexane (v/v), followed by 2 liters of EtOAc. Combine fractions to give 8.66 g (80%) of the title compound. Mass spectrum (FAB): 352[M+H]$^+$, PMR (CDCl$_3$) d 8.08(s,2), 7.91 (s,1), 7.71 (s,1), 7.42(m,1), 7.13(m,1 ), 7.85(m,2) 4.60(m,4), 4.10(m,4), 3.49(t,1), 3.14 (t,1), 3.89(m,4), 1.18(m,6).

EXAMPLE 10

Ethyl(5S-cis), and (5S-trans)-5-(2,4-Difluorophenyl) -2-oxo-5-(1H-1,2,4-triazol-1-yl)methyl]teteahydro-3-furancarboxylate Follow the procedure of Example 9, except substitute an equivalent amount of the product of Example 8 in place of the product of Example 7 to give the title compound. [PMR and mass spectra are consistent with the structure of the title compound].

EXAMPLE 11

(R)-(–)-4-(2,4-Difluorophenyl)-2-hydroxymethyl-5-[1H-(1,2,4-triazol-1-yl)]-1,4-pentanediol Dissolve 8.5 g of the product of Example 9 in 125 mL of EtOH and add 2.15 g of LiCl. Cool the stirred mixture to 0° C. and add 1.92 g of NaBH$_4$ in portions. Stir the mixture for 18 hr without further cooling. Add 125 mL of MeOH and 10 mL of $H_2O$ to the mixture and stir for 4 hr. Evaporate the mixture to dryness and extract the precipitate with warm EtOH. Evaporate the extract to dryness, add 200 mL of THF to the residue, and sonicate the stirred mixture for 15 min. Filter the mixture and evaporate the filtrate. Chromatograph the residue on silica gel, eluting with $CH_2Cl_2$—MeOH—NH$_4$OH (95:5:1) v/v/v) to obtain 3.9 g of the title compound. Mass spectrum (FAB): 314 (M+H+); PMR (DMSO) δ 8.25(s,1), 7.69(s,1), 7.35(m,1), 7.13(m,1), 6.94(m,1), 6.27 (s,1), 5.16(t,1) 4.44(m,4), 3.39(m,1), 3.20(m,1), 3.05(t,2), 2.11(m,1), 1.52(m,1).

EXAMPLE 12

(S)-(+)-4-(2,4-Difluorophenyl)-2-hydroxymethyl-5-[1H-(1,2,4-triazolyl)]-1,4-pentanediol Follow the procedure of Example 11, except substitute an equivalent amount of the product of Example 10 in place of the product of Example 9 to give the title compound. Chromatograph a portion of the crude product on silica gel eluting with $CH_2Cl_2$—MeOH—NH$_4$OH to give a product homogeneous by TLC. Dissolve the material in $H_2O$ and filter, and lyophilize the filtrate to give the title compound. [α]$_D^{25}$ +54.50 (c=1.0, MeOH)

EXAMPLE 13

(R)-(–)-4-(2,4-Difluorophenyl)-2-[[(4-methylphenyl)-sulfonyloxy]methyl]-5-[1H-(1,2,4-triazolyl)]-1,4-pentanediol-1-(4-methylbenzene)sulfonate Dissolve 4.4 g of the product of Example 11 in 50 mL of $CH_2Cl_2$-THF (1:1, v/v). Add 4.7 mL of $Et_3N$ and 180 mg of N,N-dimethylaminopyridine, and cool the solution to 0° C. Add thereto 5.9 g of p-toluenesulfonyl chloride in portions and stir the so-formed reaction mixture at 0° C. for ½ hour, and then stir it at room temperature for 5 hours. Add 100 mL of EtOAc and suction-filter the mixture. Concentrate the filtrate; add thereto 150 mL of EtOAc, and wash with 5% aqueous $KH_2PO_4$. Wash the organic layer with cold aqueous 5% NaHCO$_3$, then with saturated brine, and then dry it over anhydrous MgSO$_4$. Filter the mixture, and evaporate the filtrate. Chromatograph the residue on silica gel, eluting with EtOAC-hexane to give 6.4 g (73%) of the title compound, PMR (CDCl$_3$) δ 7.95(s,1), 7.67(m,5), 7.30(m,6) 6.70(t,2), 4.74(d,1), 4.53(d,1), 4.13(m,1), 3.97(m,1), 3.8(m,2), 2.43(s, 6), 1.95(m,2), 1.77(m,1). Mass spectrum (FAB): 622 [M+H]$^+$.

EXAMPLE 14

(S)-(+)-4-(2,4-Difluorophenyl)-2-[[(4-methylphenyl)-sulfonyloxy]methyl]-5-[1H-(1,2,4-triazolyl)]-1,4-pentanediol-1(4-methylbenzene)sulfonate Follow the procedure of Example 13 except substitute an equivalent amount of the product of Example 12 in place of the product of Example 11 to obtain the title compound, [α]$_D^{25}$+14.2° (c=1, MeOH).

EXAMPLE 15

(−)-(5R-cis)-5-(2,4-Difluorophenyl)-5-[(1H-1,2,4-triazol-1-yl)methyl]-tetrahydro-3-furanmethanol,4-toluenesulphonate Dissolve 6.3 g of the product of Example 13 in 150 mL of toluene and heat the so-formed solution to 100° C. Add 2.4 g of 60% NaH dispersion in oil portionwise, and then heat the so-formed reaction mixture at reflux until cyclization is complete (approx. 3–4 hours). Cool the mixture and decant the solution from excess NaH. Wash the solution with cold 5% aqueous KH$_2$PO$_4$. Evaporate the organic layer to form a residue and chromatograph the residue on silica gel, eluting with acetone-hexane to obtain 1.6 g (35%) of the title compound as the less polar of the two products, [α]$_D^{25}$ −39.4° (c=1, CHCl$_3$); PMR (CDCl3) δ 8.09 (s,1), 7.88 (m,3), 7.31 (m,3), 6.81(m,2), 4.52(ABq,2), 3.99(m,1), 3.85(m,1), 3.70 (m,1), 3.59(m,1), 2.49(m,2), 2.47(s,3), 1.90(m,1) Mass spectrum (FAB): 450 [M+H]$^+$.

EXAMPLE 16

(+)-(5S-cis)-5-(2,4-Difluorophenyl)-5-[(1H-1,2,4-triazol-1-yl) methyl]-tetrahydro-3-furanmethanol,4-toluenesulphonate Follow the procedure of Example 15, except substitute an equivalent amount of the product of Example 14 in place of the product of Example 13 to give the title compound, [α]$_D^{25}$+40.3° (c=0.3, CHCl3), mp 96°–98°C.

EXAMPLE 17

(−)-[(2R)-cis]-4-[4-[4-[4-[[5-(2,4-difluorphenyl)-tetrahydro-5-(1H-1,2,4-triazol-1-ylmethyl)furan-3-yl]methoxy]pheynyl-1-piperazinyl]phenyl-2,4-dihydro-3H-1,2,4-triazol-3-one, The title compound is prepared starting with the tosylate of Example 15 and 4-[4-(4-nitrophenyl)-1-piperazinyl] phenol (Example 3a of U.S. Pat. No. 4,791,111) and using the synthetic scheme outlined in Scheme V and J. Heeres, et al., *J. Med. Chem* 1984, Vol 27, p 894–900 at 898 and 900.

EXAMPLE 18

(−)-[(2R-cis]-4-[4-[4-[4-[[5-(2,4-Difluorophenyl)-Tetrahydro-5-(1H-1,2,4-Triazol-1-ylmethyl)-3-Furanyl]Methoxy]Phenyl]-1-Piperazinyl]Phenyl]-2,4-Dihydro-2-[1(S)-Methyl-2(R)-Hydroxypropyl]-3H-1,2,4-Triazol-3-One a. 2-O-SEM Ether of (2R,3R-2,3-Butanediol To a stirred solution of 4.95 g of (2R, 3R)-2,3-butanediol, (55 mmoles) and 9.3 g of SEM-Cl (55.7 mmoles) in 55 ml of anhydrous DMF at 0° C. were added in four portions 2.34 g of 60% oil-dispersed NaH (58.5 mmoles) over 10 min. The resulting mixture was stirred at 0° C. for 4 hours and at ambient temperature overnight. The turbid reaction mixture was poured onto 0.5 L of 5% KH$_2$ PO$_4$ solution and extracted with 2×300 ml of ether; the combined ethereal solution was washed once with distilled water, saturated brine, dried over MgSO$_4$ and evaporated to give a colorless liquid. Flash chromatography over 350 g silica gel with 1 L of 7% ETOAC/Hexane, 2 L of 10% ETOAC/Hexane and 1 L of 15% ETOAC/Hexane gave 1.74 g of the title compound (yield 14.4%) MS:(M+H)$^+$=221.

b. Brosylation

A mixture of 0.7 g of the 2-O-SEM ether of Example 18(a), (3.18 mmoles) and 0.97 g of 4-bromobenzenesulfonyl chloride (3.82 mmoles) in 5 ml of anhydrous pyridine was stirred under N$_2$ atmosphere at ambient temperature for 6 hours. The reddish slurry reaction mixture was diluted with 50 ml of ice-cold water, extracted with 2×25 ml of ether. The combined ethereal solution was washed with 2×25 ml of 1-% CuSO$_4$ solution, distilled water, saturated brine, dried over MgSO$_4$ and evaporated to give a reddish oily residue. Flash chromatography over 50 g silica gel with 1 L of 10% ETOAC/Hexane gave 1.02 g of the brosylate as a colorless liquid (yield 72.9%) [α]$_D^{23}$=−3.69° (CHCl$_3$; c=1)

C. Alkylation Reaction

A mixture of 0.98 g of the brosylate of Example 18(b) (2.23 mmoles), 0.69 g of the 3H-1,2,4-triazol-3-one of Example 17 (1.12 mmoles) and 0.37 g of cesium carbonate (1.12 mmoles) in 20 ml of anhydrous DMF was stirred at 80° C. under N$_2$ overnight (~20 hours). The reaction mixture was diluted with 100 ml of ice-cold water, extracted with 2×50 ml of ethyl acetate. The combined organic solution was washed once with distilled water, saturated brine, dried over MgSO$_4$ and evaporated to give a brown solid residue. Flash chromatography of the residue over 125 g silica gel with 1.2 L of 80% ETOAC/Hexane gave 0.327 g of the product as a tan solid (yield 35.7%) MS=(M+H)$^+$=81.7.

d. Acidic Hydrolysis of 18(c) to the Title Product

A mixture of 0.32 g of the SEM-ether of Example 18(c) and 6 ml of 6N HCl solution in 6 ml of methanol was stirred at ambient temperature for 4 hours and was evaporated under reduced pressure. The residue was diluted with 5 ml of ice water, carefully basified with 10% Na$_2$CO$_3$ solution until pH=8-9 was obtained. Extraction of the so-formed reaction mixture with 2×25 ml of CH$_2$ Cl$_2$ followed by washing with saturated brine, drying over MgSO$_4$ and evaporation gave a tan solid. Filtration of the tan solid through a 50 g silica gel column and elution with 0.75 L of 4% MeOH/CH$_2$Cl$_2$ gave 0.26 g of title product as a tan solid, yield 96.6%. MS=(M+H)$^+$=687; [α]$_D^{23}$=−23.65° (CHCl$_3$; c=1)

EXAMPLE 19

(−)-[(2R)-cis]-4-[4-[4-[4-[[(5-(2,4-Difluorophenyl)-Tetrahydro-5-(1H-1,2,4-Triazol-1-ylmethyl)-3-Furanyl]Methoxy]Phenyl]-1-Piperazinyl]Phenyl]-2,4-Dihydro-2-1[1(R)-Methyl-2(R)-Hydroxypropyl]-3H-1,2,4-Triazol-3-one a. Mitsunobu Reaction To a stirred solution of 0.72 g of the 2-O-SEM ether of Example 18(a) (3.27 mmoles), 2.1 g of triphenyl phosphine (8.06 g) and 1.2 g of p-nitrobenzoic acid (7.17 mmoles) in 30 ml of dry benzene at 0° C. were added, dropwise, 1.25 ml (8.06 mmoles) of diethyl azodicarboxylate ("DEAD"). The so-formed clear yellow solution became turbid and the mixture was stirred at ambient temperature for 2 hours, and mixture loaded on a 100 g silica gel column. Elution of the column with 15% ETOAC/Hexane gave 1.5 g of the 3-β-nitrobenzoate having the S absolute configuration (95% yield) MS: 219 (M$^+$−150), 252 (M$^+$−117).

b. Basic Hydrolysis of the D-Nitrobenzoate

A solution of 1.12 g of of the p-nitrobenzoate of Example 19(a) (3 mmoles) and 3.5 ml of 1N NaOH solution in 20 ml of methanol was stirred at ambient temperature for 3 hours. Solvents were evaporated and the residue was diluted with 10 ml of distilled water, and extracted with 2×20 ml of ether. The combined ethereal solution was washed once with saturated brine, dried over $MgSO_4$ and evaporated to give 0.67 g of the corresponding alcohol as a colorless liquid (~100%), which was used directly for the next reaction without further purification.

c. Brosylation, Akylation and Acidic Hydrolysis

Following the procedures of Example 18(c) and (d), the title compound was prepared in 32% overall yield in 3 steps from the products of Example 19(b) and of Example 17. MS: $[M+H]^+=687$; $[\alpha]_D^{23}=-23.65°$ ($CHCl_3$; c=1)

EXAMPLE 20

(−)-[(2R)-cis]-4-[4-[4-[4-[[5-(2,4-Difluorophenyl)-Tetrahydro-5-(1H-1,2,4-Triazol-1-ylmethyl)-3-Furanyl]Methoxy]Phenyl]-1-Piperazinyl]Phenyl]-2,4-Dihydro-2-[(S)-1-Methyl-3-Hydroxypropyl]-3H-1,2,4-Triazol-3-one a. Formation of TBDPS Ether To a solution of 0.9 g or (R)-(−)-1,3-butanediol (10 mmoles), 1.5 g of imidazole (22 mmoles) in 10 ml of anhydrous DMF at 0° C. were added 3 ml of t-butylchlorodiphenylsilane ("TBDPS") (11 mmoles) over 3 minutes. The reaction mixture was stirred at 0° C. for 4 hours, diluted with 50 ml of ice-cold water and extracted with 2×30 ml of ether. The aqueous phase was back extracted with 50 ml of ether and the combined ethereal solution was washed once with saturated brine, dried over $MgSO_4$ and evaporated to give a colorless residue. Flash chromatography over 150 g silica gel with 1.5 L of 5% EtOAC/Hexane and 1 L of 10% EtOAC/Hexane gave 2.87 g of the TBDPS ether (87.5%) MS: $[M+H]^+$: 329; $[\alpha]_D^{23}=+64°$ ($CHCl_3$; c=1)

b. Brosylation

To a solution of 0.984 g of TBDPS ether of Example 20(a) (3 mmoles) in 7 ml of anhydrous pyridine were added 0.845 g of 4-bromobenzenesulfonyl chloride (3.3 mmoles). The reaction was run and worked-up and purified in accordance with the procedure of Example 18(b) and 1.02 g of the brosylate was obtained in 61.1% yield; MS: $[M+23]^+=569/571$; $[\alpha]_D^{23}=+2.45°$ ($CHCl_3$; c=1)

c., Alkylation

The brosylate of Example 20(b), 0.95 g (1.74 mmoles) was reacted with the compound of Example 17 according to the procedure of Example 18(c) to provide 0.49 g of corresponding alkylated product, yield 60.3% MS: $(M+H)^+$ 925 $[\alpha]_D^{23}=-32.27°$ ($CHCl_3$;c=1)

d. Acidic Hydrolysis

The compound of Example 20(c), 0.32 g, (0.35 mmoels) was hydrolyzed by 6N HCl solution in accordance with the procedure of Example 18(d) to give 0.22 g of the title compound (yield 92.4%); MS: $M^+=686$; $[M+Na]^+=709$; $[\alpha]_D^{23}=-38.52°$ ($CHCl_3$; c=1)

Alternatively a solution of 0.19 g of the compound of Example 20(c) and 60 mg of tetrabutylammonium fluoride (0.23 mmoles) in 5 ml of THF was stirred at ambient temperature for 24 hours. The brown solution was concentrated to a syrup. Flash chromatography of the syrup over 50 g silica gel with 0.5 L each of 2% and 4% $MeOH/CH_2Cl_2$. gave 0.11 g of the title compound (yield 88.7%).

EXAMPLE 21

(−)-[(2R)-cis]-4-[4-[4-[4-[[5-(2,4-Difluorophenyl)-Tetrahydro-5-(1H-1,2,4-Triazol-1-Ylmethyl)-3-Furanyl]Methoxy]Phenyl]-1-Piperazinyl]Phenyl]-2,4-Dihydro-2-[(R)-1-Methyl-3-Hydroxypropyl]-3H-1,2,4-Triazol-3-one The procedures of Example 20 were followed except an equivalent amount of S-(+)-1,3-butanediol was substituted for the corresponding R enantiomer. An overall 31.8% yield of the title compound was obtained in four steps; MS=$[M+H]^+=687$.

EXAMPLE 22

(−)-[(2R)-cis]-4-[4-[4-[4-[[5-(2,4-Difluorophenyl)-Tetrahydro-5-(1H-1,2,4-Triazol-1-ylmethyl)-3-Furanyl]Methoxy]Phenyl]-1-Piperazinyl]Phenyl]-2,4-Dihydro-2-[1(S)-Methyl-2(S)-Hydroxypropyl]-3H-1,2,4-Triazol-3-one a. Benzylation To a solution of 10 g of (2R, 3R)-(−)-2,3-butanediol (111 mmoles) in 40 ml of anhydrous $CH_2Cl_2$ and 80 ml of cyclohexane at 0° C. were added 1 ml of trifluoromethanesulfonic acid (TfOH), followed by dropwise addition of 21 ml of benzyl trichloroacetimidate (113 mmoles). The resulting slurry was stirred at ambient temperature overnight, diluted with 125 ml of hexane and filtered. The combined filtrate was concentrated to a yellow syrup. Flash chromatography of the yellow syrup over 250 g silica gel with 1.5 L of 7% ETOAC/Hexane, 2 L of 15% ETOAC/Hexane and 2 L of 25% ETOAC/Hexane, 1.5 L of 10% $MeOH/CH_2Cl_2$ gave 11.88 g of the 2-monobenzyl ether of the starting material (74.5% yield) and 2.03 g of unreacted starting material MS: $[M+H]^+$: 181.

b. Mitsunobu Reaction

The 2-monobenzyl ether of Example 22(a), 5.4 g, was converted into 6.6 g of the 3-benzoate ester (yield 66.9%) by Mitsunobu reaction in accordance with the procedure of Example 19(a); MS: $[M+H]^{30}=330$.

c. Alkaline Hydrolysis

The 5.3 g of the product of Example 22(b) was subjected to alkaline hydrolysis according to the procedure of Example 19(b) to give 2.33 g of the 2-monobenzyl ether of (2R,3S)-2,3-butanediol (yield 80.3%) $(M+H)^+=181$; $[\alpha]_D^{23}=-23.75°$ ($CHCl_3$; c=1)

d. Formation of the SEM Ether

To a stirred solution of 3.14 g of the product of Example 22(c) (17.44 mmoles) and 3.8 ml of di-isopropylethylamine (2.82 g, 21.8 mmoles) in 30 ml of anhydrous $CH_2Cl_2$ at ambient temperature were added 3.8 ml of SEM-Cl (3.64 g, 21.8 mmoles) in one portion. Fuming formed and the resulting yellow solution was stirred for 20 hours. The orange-colored reaction mixture was evaporated under reduced pressure and the solid residues were partitioned between ether and water. The ethereal solution was washed once with distilled water, saturated brine, dried over mg 504 and concentrated to give the crude product. Flash chromatography of the crude product over 200 g silica gel with 2 L of 3% ETOAC/Hexane gave 5.3 g of the 3-O-SEM ether of the product of Example 22(c) (98% yield) as a colorless liquid; MS: $[M+H]^+=311$.

e. Hydrogenolysis

A mixture of 5.25 g of the product of Example 22(d) (16.94 mmoles) and 0.5 g of 10% Pd/C in 150 ml of methanol was hydrogenated under atmospheric pressure for 6 hours. Catalysts were filtered and washed with additional methanol. The combined filtrate was concentrated to give a colorless liquid. Flash chromatography of the liquid over 100 g silica gel with 2 L of 10% ETOAC/hexane 3.53 g of the free alcohol (yield 95%) as a colorless liquid; MS: 174, 103.

f. Brosylation

The product of Example 22(e) 1 g was converted into 1.52 g of the corresponding brosylate in 76.2% yield in accordance with the procedure of 18(b); $[\alpha]_D^{23}=-1.53°$ ($CHCl_3$; c=1)

g. Alkylation Reaciton

The brosylate of Example 22(f), 1.48 g of was reacted with the product of Example 17 to give 0.75 g of the 2-alkylated triazol-3-one (yield 54.3%); $[\alpha]_D^{23}=-32.69°$ (CHCl$_3$; c=1)

h. Acidic Hydrolysis

Hydrolysis of 0.7 g of the product of Example 22(g) in accorcdance with the procedure of Example 18(d) gave 0.51 g of the title compound as a cream-colored solid (yield 86.7%); $[\alpha]_D^{23}=-32.69°$ (CHCl$_3$; c=1)

EXAMPLE 23

(−)-[(2R)-cis]-4-[4-[4-[4-[[5-(2,4-Difluorophenyl)-Tetrahydro-5-(1H-1,2,4-Triazol-1-ylmethyl)-3-Furanyl]Methoxy]Phenyl]-1-Piperazinyl]Phenyl]-2,4-Dihydro-2-[1(R)-Methyl-2(S)-Hydroxypropyl]-3H-1,2,4-Triazol-3-one a. Mitsunobu Reaction

The product of step of Example 22 (1.99 g, 9.05 mmoles) was reacted with p-nitrobenzoic acid in accordance with the procedure Example 19(a) to give 3.3 g of product (yield 98.8%); MS=[M+H]$^+$=221.

b. Alkaline Hydrolysis

The product of step (a) of this Example (2.36 g, 6.4 mmoles) was hydrolyzed by 7 ml of 1N NaOAc to give 1.18 g of the 3-O-SEM ether of (2S,3S)-2,3-butanediol (yield 83.7%). MS: [M+H]$^+$=221 $[\alpha]_D^{23}$=+55.15° (CHCl$_3$; C=1).

c. Brosylate Formation

The product of step (b) of this Example (1.15 g were converted into the brosylate in accordance with the procedure of Example 18(b) to give 3.47 g of the brosylate (yield 97.7%).

d. Alkylation and Acidic Hydrolysis

The procedures of Example 18(c) and (d) were followed except the product of Example 23(c) was substituted for that of 18(b) to give the title compound.

EXAMPLE 24

(2R-cis)-4-[4-[4-[4-[[-5-(2,4-difluorophenyl)-tetrahydro-5-(1H-1,2,4-triazol-1-ylmethyl)furan-3-yl]methoxy]phenyl]-1-piperazinyl]phenyl]2-4-dihydro-2-[(S)-1-ethyl-2(S)-hydroxypropyl]-3H-1,2,4-Triazol-3-One a.

The methyl ester of (S)-lactic acid was converted into the corresponding benzyloxymethyl ether in accordance with the procedure of W. C. Still, et al. *Tetrahedron Letters*, 21, 1035–1038 (1980).

b. Reduction to the Aldehyde

DIBAL-H, 37.7 ml of a 1M solution, was added dropwise to a stirred solution of 7.67 g of the ester of step (a) of this Example in toluene at −78° C. (dry ice/acetone bath) under an atmosphere of nitrogen. After 6 min. methanol (10 ml) followed by an aqueous solution of Rochelles salt were added. After warming to room temperature the moisture was partitioned between ETOAc and water. The organic phase was separated, washed with water, dried (MgSO$_4$) and concentrated to produce the crude aldehyde which was used in the next step without purification.

b. Grignard Step

The THF solution of 80 ml of 1 molar solution of the ethyl magnesium bromide Grignard reagent was added dropwise to a stirred THF solution of the crude aldehyde obtained from step (b) of this Example at −78° C. (dry ice/acetone bath) under an atmosphere of nitrogen. After the addition was complete, the resulting mixture was allowed to warm slowly to room temperature overnight and stirred for a further period of 48 h. An aqueous solution of Rochelles salt was added and then the resulting mixture was partitioned between acetone and water. The organic phase was separated, washed with water, dried (MgSO$_4$) and concentrated. The residue was purified by column chromotography on silica gel using ETOAC/Hexane (1:10) as eluant to give (i) non-polar alcohol (2S,3S) 2.31 g; 31%, as a colorless oil.

(ii) a mixture of both alcohols, 1.23 g; 41% and (iii) polar alcohol (2S,3R) 1.23 g; 16%, as a colorless oil.

c. Brosylation of Polar Alcohol

4-Bromobenzenesulphonyl chloride (1.035 g, 4.1 mmoles) was added to a stirred solution of (0.605 g, 2.7 mmoles) the polar (2S, 3R) alcohol of step (b) of this Example and 2.20 g (5.9 mmoles) of DMAP in CH$_2$Cl$_2$ at room temperature under an atmosphere of nitrogen. The resulting mixture was stirred for 12 h. and then partitioned between ETOAC and water. The organic phase was separated, washed with water, dried and concentrated. The residue was purified by column chromatography on silica gel using ETOAC/Hexane (1:10) as eluant to give the desired brosylate (85%) as a colorless oil.

d. Alkylation and Acidic Hydrolysis

The procedures of Example 18(c) and (d) were followed except the (2S, 3R) bosylate of step (c) of this Example was substituted for that used in Example 18(c). The acidic hydrolysis produced the title compound as a white solid, mp 170°–172° C.

EXAMPLE 25

(2R-cis)-4-[4-[4-[[-5-(2,4-difluorphenyl)-tetrahydro-5-(1 H-1,2,4-triazol-1-ylmethyl)furan-3-yl]methoxy]phenyl]-1-piperazinyl]phenyl]-2,4-dihydro-2-[(R)-1-ethyl-2(S)-hydroxpropyl]-3H-1,2,4-triazol-3-one The procedures of Example 24 were followed except the non-polar (2S,3S) alcohol from step (b) of Example 24 was converted into the (2S,3S)-3-brosylate. Alkylation of the brosylate followed by acidic hydrolysis of the SEM protecting group in accordance with the procedures of Example 24(d) provided the title compound.

EXAMPLE 26

(2R-cis)-4-[4-[4-[[-5-(2,4-difluorphenyl)-tetrahydro-5-(1 H-1,2,4-triazol-1-ylmethyl)furan-3-yl]methoxy]phenyl]1-piperazinyl]phenyl]2,4-dihydro-2-[(R)-1-ethyl-2(R)-hydroxpropyl]-3H-1,2,4-triazol-3-One The procedures of Example 24 were followed except the methyl ester of (R) lactic ester was substituted for the methyl ester of (S)-lactic acid in step (a) of Example 24. The (2R, 3S) alcohol was used in steps (c) and (d) to provide the title compound.

EXAMPLE 27

(2R-cis)-4-[4-[4-[[-5-(2,4-difluorphenyl)-tetrahydro-5-(1 H-1,2,4-triazol-1-ylmethyl)furan-3-yl]methoxy]phenyl]1-piperazinyl]phenyl]2,4-dihydro-2-[(S)-1-ethyl-2(R)-hydroxpropyl]-3H-1,24-triazol-3-One The procedures of Example 26 were followed except the (2R, 3R) alcohol was used in steps (c) and (d) to provide the title compound.

EXAMPLE 28

(2R-cis)-4-[4-[4-[4-[[-5-(2,4-difluorphenyl)-tetrahydro-5-(1 H-1,2,4-triazol-1-ylmethyl)furan-3-yl]methoxy]phenyl]1-piperazinyl]phenyl]2,4-dihydro-2-[(R)-1-ethyl-3-hydroxpropyl]-3H-1,2,4-triazol-3-One a. Reduction To methyl (3R)-hydroxyvalerate (5.289, 40.0 mmoles) dissolved in 100 ml of anhydrous THF at 0°–5° C. was added dropwise 60 ml of a 1M THF solution of LiAlH$_4$ (60 mmoles). The solution was allowed to warm to ambient temperature and to the so-formed mixture was added sequentially, 2.5 mL of water, dropwise, 2.5 mL of 15% NaOH and 7.5 mL of water. The so-formed reaction mixture was stirred at ambient temperature for 4 h. The inorganic solids were removed by filtration and the filtrate was evaporated to give 4.31 g of (3R)-1,3-pentanediol.

b. 1-O-SEM Ether Formation

The procedure of Example 18(a) was followed except an equivalent quantity of the product of step (a) of this Example was substituted for the (2R, 3R)-2,3-butanediol to provide the title compound.

c. Mitsunobu Reaction

The procedure of Example 19(a) was followed except that an equivalent quantity of the product of step (b) of this Example was substituted for the 2-SEM ether of (2R,3R)-2,3-butanediol to give 3.34 g of the corresponding p-nitrobenzoate.

d. Basic Hydrolysis

The procedure of Example 19(b) was followed except that an equivalent quantity of the p-nitrobenzoate ester of step (c) of this Example was used to provide 1.88 g of the 1-O-SEM ether of (3S)-1,3-pentanediol.

e. Brosylation, Alkylation and Acid Hydrolysis

The procedures of Example 18 (b), (c), and (d) were followed except that an equivalent quantity of the product of step (d) of this Example was substituted for the corresponding 1-O-SEM ether of (2R, 3R) 2,3-butanediol used in Example 19(b) to produce 1.04 g of the title compound of this Example [α]$_D^{23}$=−8.42° (CHCl$_3$; c=1)

EXAMPLE 29

(2R-cis)-4-[4-[4-[4-[[-5-(2,4-difluorphenyl)-tetrahydro-5-(1 H-1,2,4-triazol-1-ylmethyl)furan-3-yl]methoxy]phenyl]1-piperazinyl]phenyl]2-4-dihydro-2-[(S)-1-ethyl-3-hydroxpropyl]-3H-1,2,4-triazol-3-One The procedures (a) and (b) of Example 28 were followed to produce the 1-O-SEM-(3R)-1,3-pentanediol which was converted directly into the 3R brosylate by following the procedures of Example 18(b). The 3R brosylate was used to alkylate the product of Example 17 in accordance with the procedures of Example 18(c). The so-formed product was subjected to acidic hydrolysis in accordance with the procedures of Example 18(d) to provide 368 mg (90% yield) of the title compound; [α]$_D^{23}$=−47.11° (CHCl$_3$; c=1)

EXAMPLE 30

(2R-cis)-4-[4-[4-[4-[[-5-(2,4-difluorphenyl)-tetrahydro-5-(1 H-1,2,4-triazol-1-ylmethyl)furan-3-furanyl]methoxy]phenyl]1-piperazinyl]phenyl]2-4-dihydro-2-[1-hydroxy-(2R)-butyl]-3H-1,2,4-triazol-3-One a. Preparation of (2S)-1,2,-butanediol A solution of (2S)-3-butene-1,2-diol which was purchased from Eastman Kodak, (3 g, 0.034 mmoles) in 40 mL of ethanol was hydrogenated in the presence of 300 mg of 10% Pd/C overnight. The so-formed reaction mixture was filtered through celite. The so-formed filter cake was washed with ethanol and the combined filtrates were evaporated to provide 2.08 g (68% yield) of the title compound.

b. 1-O-SEM ether formation, brosylaton, alkylation and acidic hydrolysis

The procedures of Example 18(a)–(d) were followed except that an equivalent amount of the product of step (a) of this Example was substituted for the (2R, 3R) 2,3-butanediol of Example 18 to provide the title compound [α]$_D^{23}$=−24.3° (CHCl$_3$; c=1)

EXAMPLE 31

(2R-cis)-4-[4-[4-[4-[[-5-(2,4-difluorphenyl)-tetrahydro-5-(1H-1,2,4-triazol-1-ylmethyl)furan-3-furanyl]methoxy]phenyl]1-piperazinyl]phenyl]2-4-dihydro-2-[1-hydroxy-(2S)-butyl]-3H-1,2,4-triazol-3-one The procedures of Example 30 were followed except that an equivalent quantity of (2R)-3-butene-1,2-diol (available from Eastmand Kodak) was substituted for (2S)-3-butene-1,2-diol in step (a) of Example 30. The procedures of Example 30(b) were there after followed to produce the title compound [α]$_D^{23}$=−29.4° (CHCl$_3$; c=1)

EXAMPLE 32

(−)(2R-cis)-4-[4-[4-[4-[[-5-(2,4-difluorphenyl) tetrahydro-5-(1H-1,2,4-triazol-1-ylmethyl)furan-3-yl]methoxy]-phenyl]1-piperazinyl]phenyl]-2,4-dihydro-2-[(S)-1-ethyl-2(S)-hydroxypropyl]-3H-1,2,4-triazol-3-one a. (S)-2-(benzyloxy) propionaldehyde by selective reduction of (S)-(O-benzyl) lactic acid pyrrolidine amide:

To a solution of the S-(O-benzyl)lactic acid pyrrolidene amide prepared in accordance with the procedure of Tetrahedron, 1989, vol. 45, pages 57–67 (5 g, 0.0214 mol.) dissolved in 20 ml of toluene cooled to in a ice methanol bath was added slowly with stirring 4.25 ml or RED-AL (3.4M solution of sodium bis(2-methoxyethoxy) aluminum hydride) in toluene available from Aldrich Chemical Catalogue #19, 619-3). The solution was stirred fro 5 hrs., quenched with 2.5 ml of acetone and thereafter with 35 ml of 2NHCl. The so-formed mixture was extracted with EtoAc. The organic extracts were washed with water, NaHCO$_3$ and brine, dried over Na$_2$SO4 and evaporated to give the titled product.

b. (S)-2-(Benzyloxy)-N-(Formylamino) propanimine.

The propionaldehyde of step (a) (1 g, 16.09 mml) was added dropwise to a solution of formyl hydrazine (0.73 g, 12.18 mmol) dissolved in 5 ml of methanol. The so-formed reaction mixture was stirred overnight. The solvent was removed by evaporation and the so-formed residue was stirred with ethyl ether. The undissolved excess formyl hydrazine was removed by filtration and the ether was removed to provide a residue which was chromatographed on silica gel(/) using 20% EtoAc: hexane (v:v) to give 805 mg of the title product as a light yellow waxy solid having strong UV activity; ms [M +H]$^+$=207.

c. 2-[3-(2S, 3S)-2-(Benzyloxy)pentyl]formic acid hydrazide

Ethylmagnesium bromide (1.3 ml, 3.9 mmol, 3.0 molar in ethyl ether) was added to a stirred solution of 200 mg, 0.97 mmol of the propanimine of step (b) in 10 ml of ethyl ether at 0° C. The so-formed reaction mixture was stirred overnight at room temperature and quenched with water. The organic layer was separated and the solvent removed to provide a residue which was chromatographed on silica gel using 30 to 50% of EtoAc:hexane (v:v) to provide 113 mg; (50% yield) of the title compound as an oil. The ratio of S,S isomer: S,R isomer in the product was 94:6. When the reaction was repeated in the presence of 1.2 equivalent of bis(trimethylsilyl) acetamide the S,S:S,R ratio improved to 99:1 MS: $[M+H]^+=237$ d. Cyclization Reaction A solution of 156.3 mg, 0.66 mmol of the product of step (c) and 400 mg 0.60 mmol of 17F of Scheme V and 1 mole of DBU (1,8-diaza bicyclo [5.4.0]undec-7-ere) in volume was stirred at 80° C. for six hours; the temperature was raised to 100° to 110° C. and stirring was continued at this temperature overnight. The reaction mixture was allowed to cool to room temperature and the stirring was continued over the weekend. The solvent was removed by evaporation and the crude product was purified on preparative TLC (80% EtoAc) hexane, v:v) to provide 200 mg of the benzyl ether of the title product of this example as a foamy solid; MS:$[M+H]^+=792$ This cyclization reaction is the invention of Mergelsberg, Gala et. al. which is disclosed in commonly-owned U.S. patent application Ser. No. (attorney's Docket #CD0475), filed Apr. 19, 1995.

e. Hydrogenolysis

To the solution of the benzyl ether (190 mgs, 0.24 mmol) of step d dissolved in 10 ml of methanol was added 40 mg of Pd black on carbon and 4 ml of formic acid. The reaction flask was sealed with a ballon and heated at 60° C. for four hours. The catalyst was removed by filtration through a celite cake and the filtrate was poured into cold water. The pH of the so-formed solution was adjusted to a value of 4 to 5 with amonia. The so-formed mixture was extracted with EtoAc. The organic layer was separted and dried over $Na_2SO_4$. The solvent was removed to provide a crude product which was purified on preparative TLC (5% methanol: $CH_2CL_2$, v:v) to give 95 mg of the title compound of this example. (57% yield) as a tan solid. MS: $[M+H]^+=701$. $[\alpha]=-28.4$ ($c,=1.0$, $CHCl_3$)

EXAMPLE 33

(−)-[(2R)-cis[-4-[4-[4-[4-[[5-(2,4-Difluorophenyl)-Tetrahydro-5-(1H-1,2,4-Triazol-1-ylmethyl)-3-Furanyl]Methoxy]Phenyl]-1-Piperazinyl]Phenyl]-2, 4-Dihydro-2-[1(S)-Ethyl-2(S)-Hydroxypropyl]-3H-1,2,4-Triazol-3-one. Ester with Glycine (as Hydrochloride)

A. To a solution of N-Cbz-glycine (315 mg), N,N-dimethylaminopyridine (DMAP, 200 mg), and compound of Example 24 (900 mg) in $CH_2Cl_2$ (50 mL) at 0° C., add dicyclohexylcarbodiimide (DCCD, 290 mg). Stir the solution at 0° C. for 30 min., then at room temperature for 1 hr. Add additional N-Cbz-glycine (700 mg) and then increments of DCCD at 20 min. intervals until the reaction is complete by TLC. Pour the reaction mixture into 5% aqueous $KH_2PO_4$ and extract with EtOAc. Wash the EtOAc extracts three times with 5% aqueous $KH_2PO_4$, then with brine, and dry the extracts over anhydrous $MgSO_4$. Filter, evaporate the filtrate, and chromatograph the residue to obtain the N-Cbz-glycinyl ester (1.3 g), [Mass spec. found: (FAB) 892 $(M+H^+)$.]

B. Stir a solution of the N-Cbz-glycinyl ester of step A above in 100 mL MeOH-96% HCOOH (10:1) in sealed flask with a safety valve. Add 30 mg increments of palladium black at 30 min intgervals until the reaction is complete by TLC (6–14 hr.). Suction-filter the mixture, add 12 N HCl (0.5 mL) to the filtrate and evaporate the so-formed mixture to dryness, Add water (100 mL) and activated carbon (0.8 g) to the residue, suction-filter on a 0.45µ nylon membrane. Lyophilize the filtrate to provide 356 mg of the title compound. [Mass spec. found: (FAB) 795 $(M+H^+)$.]

EXAMPLE 34

Follow the procedure of Example 33 except substitute an equivalent amount of any other N-carbonbenzoxy or N-tert-butoxycarbonyl protected natural amino acid to obtain the corresponding natural c-amino acid ester hydrochloride of the compound of Example 32.

EXAMPLE 35

(−)-[(2R)-cis]-4-[4-[4-[4-[[5-(2,4-Difluorophenyl)-Tetrahydro-5-(1H-1,2,4-Triazol-1-ylmethyl-3-Furanyl]Methoxy]Phenyl]-1-Piperazinyl]Phenyl]-2, 4-Dihydro-2-[1(S)-Ethyl-2(S)-Hydroxypropyl]-3H-1,2,4-Triazol-3-one. Ester with 2,4-Diaminobutanoic acid (as Di-Hydrochloride salt)

Follow the procedure of Example 33 except substitute an equivalent quantity of N,N'-dicarbobenzoxy 2,4-diaminobutanoic acid for N-Cbz-glycine to obtain the title compound.

EXAMPLE 36

(−)-[(2R-cis]-4-[4-[4-[4-[[5-(2,4-Difluorophenyl-Tetrahydro-5-(1H-1,2,4-Triazol-1-ylmethyl)-3-Furanyl]Methoxy]Phenyl]-1-Piperazinyl]Phenyl]-2, 4-Dihydro-2-[1(S)-Ethyl-2(S)-Hydroxypropyl]-3H-1,2,4-Triazol-3-one. Ester with L-Alanine (as Hydrochloride salt)

Follow the procedure of Example 33 except substitute an equivalent quantity of N-carbobenzoxy-L-alanine for N-Cbz-glycine to obtain the title compound.

EXAMPLE 37

The preferred compounds of formula 20F prepared in accordance with the procedures of Examples 1–32 and Schemes I–VI are listed hereinbelow:

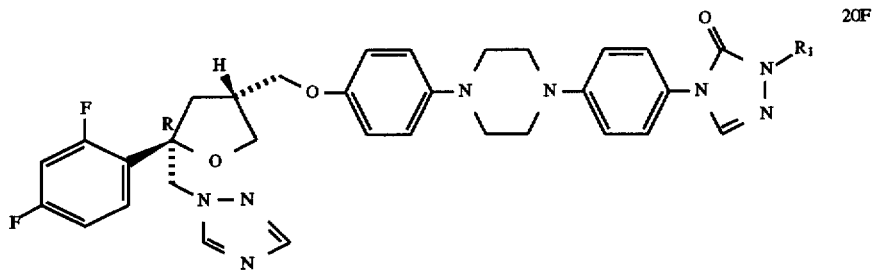

wherein R₁ is:

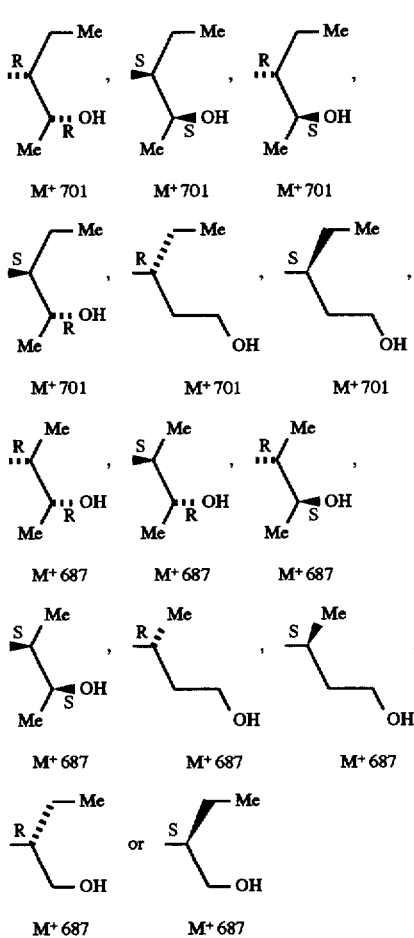

the above-listed compound 20F wherein R₁=

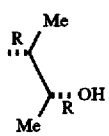

was prepared by substitution of an equivalent amount of (2R,3R)-2,3-butanediol for the 2-monobenzyl ether of (2R,3S) butanediol used in step d of Example 22. The product so formed was treated in accordance with the procedures of steps f, g, and h of Example 22. The above-listed compound 20F wherein R₁= was prepared by substitution of an equivalent amount of the 2-O-SEM ether of 2R,3R butanediol for the starting material used in step d of Example 22. The product so formed was thereafter treated in accordance with the procedures of steps c, f, g, and h of Example 22.

What is claimed is:

1. A compound represented by the formula I

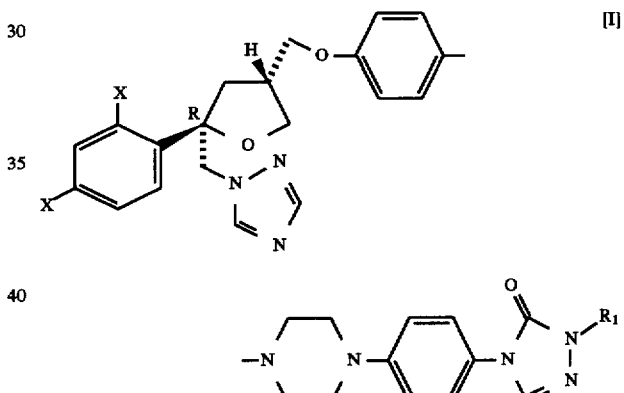

wherein X is independently both F or both Cl or one X is independently F and the other is independently Cl;

R₁ is a straight or branched chain ($C_4$ to $C_5$) alkyl group substituted by a hydroxy group or a pharmaceutically acceptable salt thereof.

2. A compound of claim 1 wherein R₁ is a hydroxy-substituted $C_4$- or $C_5$-alkyl group selected from:

—*CH(C₂H₅)*CH(R₄)CH₃, —*CH(C₂H₅)CH₂CH₂R₄, —(CH₂)₂—*CH(R₄)C₂H₅, —*CH(CH₃)*CH(R₄)CH₃, —*CH(C₂H₅)CH₂R₄ and —*CH(CH₃)CH₂CH₂R₄ wherein R₄ is OH and the carbons with the asterisk(*) have the R or S absolute configuration or a pharmaceutically acceptable salt thereof.

3. The compound of claim 1 wherein R₁ is a $C_4$ alkyl group substituted by a hydroxy group.

4. The compound of claim 1 wherein R₁ is a $C_5$ alkyl group substituted by a hydroxy group.

5. A compound represented by formula III

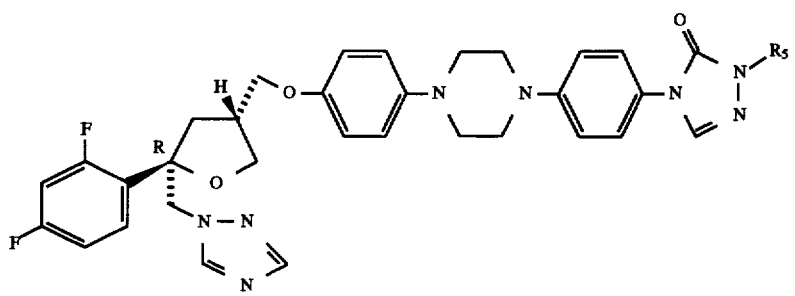

wherein R₅ is

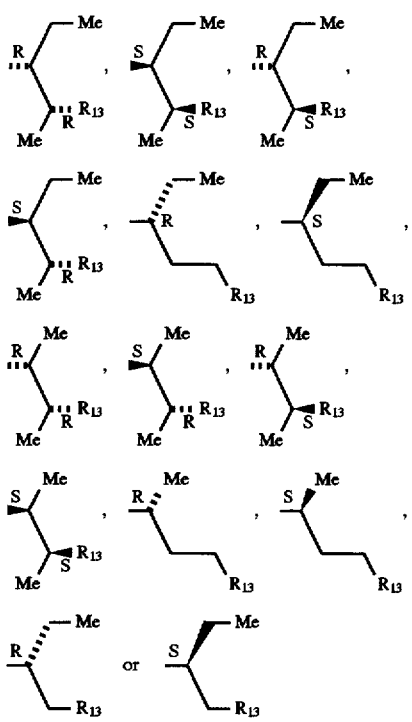

wherein $R_{13}$ is a hydroxy group, or a pharmaceutically acceptable salt thereof.

6. A compound represented by the formula IV

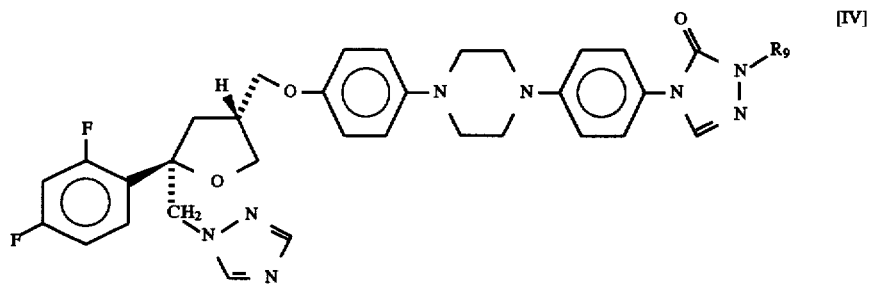

wherein $R_9$=—*CH(C₂H₅)CH(R₆)CH₃ or —*CH(CH₃)CH(R₆)CH₃
wherein $R_6$ is OH or a pharmaceutically acceptable salt thereof.

7. A pharmaceutical composition for treating or preventing fungal infection comprising an antifungally effective amount of a compound of claim 1 together with a pharmaceutically acceptable carrier therefor.

8. A method of treating and/or preventing fungal infections in a mammal afflicted with same which comprises administering an antifungally effective amount of a compound of claim 1 sufficient for such treating or preventing.

9. The pharmaceutical composition of claim 1 wherein the mode of administration is oral or parenteral.

* * * * *